(12) United States Patent
Otsuka et al.

(10) Patent No.: US 7,094,512 B2
(45) Date of Patent: Aug. 22, 2006

(54) ELECTROPHOTOGRAPHIC PRINTING METHOD, MONOAZO IRON COMPLEX COMPOUND, CHARGE CONTROLLING AGENT USING THE SAME AND TONER USING THE CHARGE CONTROLLING AGENT

(75) Inventors: Hideyuki Otsuka, Fukushima (JP); Kazuo Nemoto, Fukushima (JP); Shinji Otani, Shizuoka (JP); Noriyuki Suzuki, Fukushima (JP); Eisuke Yamada, Fukushima (JP); Masaki Okubo, Fukushima (JP)

(73) Assignee: Hodogaya Chemical Co., Ltd., Kawasaki (JP)

( * ) Notice: Subject to any disclaimer, the term of this patent is extended or adjusted under 35 U.S.C. 154(b) by 248 days.

(21) Appl. No.: 10/714,853

(22) Filed: Nov. 18, 2003

(65) Prior Publication Data

US 2004/0191660 A1    Sep. 30, 2004

(30) Foreign Application Priority Data

| Mar. 31, 2003 | (JP) | ............................. 2003-096578 |
| Jul. 24, 2003 | (JP) | ............................. 2003-201262 |
| Aug. 11, 2003 | (JP) | ............................. 2003-207208 |
| Oct. 16, 2003 | (JP) | ............................. 2003-356674 |

(51) Int. Cl.
*G03G 9/08* (2006.01)

(52) U.S. Cl. ............................. 430/108.23; 430/109.3

(58) Field of Classification Search ........... 430/108.23, 430/109.3; 534/710
See application file for complete search history.

(56) References Cited

U.S. PATENT DOCUMENTS

| 5,204,453 A * | 4/1993 | Chambon et al. ........... 534/602 |
| 5,529,872 A | 6/1996 | Grychtol et al. |
| 6,168,895 B1 * | 1/2001 | Metz et al. ............ 430/108.23 |
| 2001/0004667 A1 | 6/2001 | Okubo et al. |
| 2002/0156161 A1 | 10/2002 | Koshida et al. |

FOREIGN PATENT DOCUMENTS

| EP | 0 977 093 | 2/2000 |
| JP | 43-17955 | 7/1968 |
| JP | 43-27596 | 11/1968 |
| JP | 57-167033 | 10/1982 |
| JP | 60-106859 | 6/1985 |
| JP | 60-107655 | 6/1985 |
| JP | 61-155464 | 7/1986 |
| JP | 62-225583 | 10/1987 |
| JP | 2-305832 | 12/1990 |
| JP | 5-192638 | 8/1993 |
| JP | 7-32535 | 2/1995 |
| JP | 7-32538 | 2/1995 |
| JP | 7-32539 | 2/1995 |
| JP | 7-32540 | 2/1995 |
| JP | 7-227570 | 8/1995 |
| JP | 8-500912 | 1/1996 |
| JP | 10-48875 | 2/1998 |
| JP | 11-020317 | 1/1999 |
| JP | 11-20317 | 1/1999 |
| JP | 11-133670 | 5/1999 |
| JP | 11-20317 | * 11/1999 |
| JP | 2001-194830 | 7/2001 |
| JP | 2001-356526 | 12/2001 |
| JP | 2002-82480 | 3/2002 |
| JP | 2002-82481 | 3/2002 |
| JP | 2002-264521 | * 9/2002 |
| JP | 2003-15364 | 1/2003 |
| JP | 2003-231843 | 8/2003 |
| JP | 2004-2618 | 1/2004 |
| WO | WO 94/03841 | 2/1994 |
| WO | WO 03/098617 | 11/2003 |

* cited by examiner

*Primary Examiner*—John L Goodrow
(74) *Attorney, Agent, or Firm*—Oblon, Spivak, McClelland, Maier & Neustadt, P.C.

(57) ABSTRACT

An electrophotographic printing method which comprises using a charge controlling agent containing a monoazo iron complex compound of the formula (1) as an effective component,

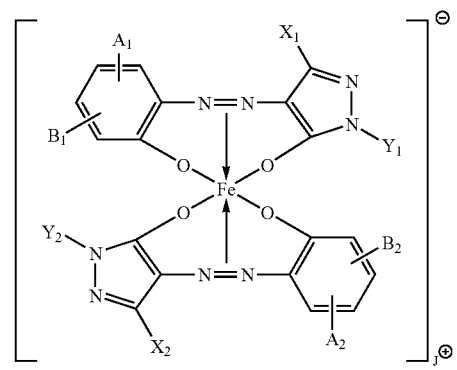

wherein $A_1$, $A_2$, $B_1$ and $B_2$ are respectively independently H, an alkyl group or a halogen atom, J is H, an alkali metal, $NH_4$ or an alkylammonium, they may be two or more kinds, $X_1$ and $X_2$ are respectively independently H, an alkyl group or a halogen atom, and $Y_1$ and $Y_2$ are respectively independently H, an alkyl group or an aromatic group which may have a substituent, provided that a case in which $A_1$, $A_2$, $B_1$, $B_2$, $X_1$, $X_2$, $Y_1$, and $Y_2$ are hydrogen at the same time is excluded.

29 Claims, 14 Drawing Sheets

ELECTROPHOTOGRAPHIC PRINTING METHOD, MONOAZO IRON COMPLEX COMPOUND, CHARGE CONTROLLING AGENT USING THE SAME AND TONER USING THE CHARGE CONTROLLING AGENT

BACKGROUND OF THE INVENTION

1. Field of the Invention

The present invention relates to a charge controlling agent and a negatively chargeable toner containing the charge controlling agent used for an image-forming apparatus for developing an electrostatic latent image in the fields of electrophotography, electrostatic recording and the like.

2. Discussion of Background

In an image-forming process by electrophotographic system, an electrostatic latent image is formed on a photosensitive material comprising an inorganic or organic material, developed by a toner, transferred onto a paper, a plastic film or the like, and fixed thereon to obtain a visible image. The photosensitive material has negative chargeability or positive chargeability depending on its structure, and when an image part is left as a latent image by exposure to light, the latent image is developed by a reversely charged toner. On the other hand, when an image part is destaticized to carry out reverse development, the development is carried out with a charged toner the same charge.

A toner comprises a binder resin, a colorant and other additives. In order to impart a preferable chargeability (charging speed, charging level, charging stability or the like), a stability as a lapse of time, an environmental stability and the like, a charge controlling agent is generally added to the toner. Properties of the toner are greatly improved by adding the charge controlling agent.

Examples of a charge controlling agent having an effect of imparting a negative charge controlling property conventionally proposed and practiced, include a monoazo metal complex compound having chromium as a center metal, a monoazo metal complex compound having iron as a center metal, and a metal complex of an alkyl salicylic acid or aromatic carboxylic acid or their salt.

However, these charge controlling agents have such defects that a tribo-chargeability or an affinity to a binder resin of a toner is unsatisfactory, that a quick chargeability (charge up speed) is unsatisfactory, that an initial copy image is not clear, and that a quality of a copy image is easily variable during continuous copying operation. Also, a charge controlling agent comprising a metal complex of an alkyl salicylic acid or aromatic oxycarboxylic acid or its salt has such defects that a toner chargeability is largely varied depending on environmental conditions and that an image quality is largely varied depending on a season factor.

Among monoazo chromium complex compounds, there is a compound solving a part of these problems, but there is a possibility that a minor amount of noxious hexavalent chromium is formed at the time of burning and discarding and it is worried to provide a bad influence on environments or human bodies. Accordingly, it has been demanded to provide a charge controlling agent using a safer metal and having satisfactory properties.

JP-A-61-155464 discloses a toner using a charge controlling agent containing iron as a center metal. Although this is a negatively chargeable charge controlling agent containing no chromium as a center metal, this charge controlling agent provides a practical charged amount (at least −10 μc/g) but a quick chargeability is poor as compared with a chromium complex and there is a problem that a chargeability is lowered under a high humidity environment. Also, JP-A-8-500912 discloses some azo iron complexes, but all of azo complexes having satisfactory performances have a plurality of nitro groups and therefore there are always risks of combustion and explosion during synthesizing these compounds. Particularly when the center metal is iron, a risk of occurrence of combustion and explosion is very high and drying and pulverizing steps are very dangerous operations. Also, since a pulverized type toner is generally kneaded by an extruding kneader and is pulverized, there is a possibility of causing powder explosion at the time of preparing the toner. When using chromium at a center metal, a possibility of causing combustion and explosion is lowered as compared with iron, but an azo chromium complex having a nitro group obtained in this case corresponds to a self-reactive material (Class 5 dangerous material).

SUMMARY OF THE INVENTION

An object of the present invention is to provide a novel monoazo iron complex compound, particularly to provide a charge controlling agent excellent in a charge-imparting effect, containing no noxious metal like chromium and having no fear of such combustion or explosion as caused by a compound containing a nitro group, and further to provide a negatively chargeable toner containing said charge controlling agent and consequently having a high charging performance.

In order to achieve the above object, the present inventors have studied intensively, and the present invention has been accomplished on the basis of this study. The essential features of the present invention are illustrated below.

1. An electrophotographic printing method which comprises using a charge controlling agent containing a monoazo iron complex compound of the formula (1) as an effective component,

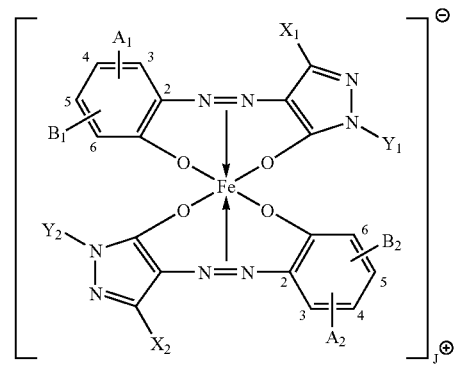

wherein $A_1$, $A_2$, $B_1$ and $B_2$ are respectively independently H, an alkyl group or a halogen atom (the alkyl group has a carbon number of preferably 1 to 8, more preferably 1 to 4, and the halogen atom is preferably chlorine), J is H, an alkali metal, $NH_4$ or an alkylammonium, they may be two or more kinds (an alkyl group of the alkyl ammonium has a carbon number of 1 to 12, preferably 3 to 8, and a nitrogen atom may have 1 to 4 same or different alkyl groups bonded thereon), $X_1$ and $X_2$ are respectively independently H, an alkyl group or a halogen atom, and $Y_1$ and $Y_2$ are respectively independently H, an alkyl group (the alkyl group has a carbon number of preferably 1 to 8, more preferably 1 to 4) or an aromatic group which may have a substituent, provided that a case in which $A_1, A_2, B_1, B_2, X_1, X_2, Y_1,$ and $Y_2$ are hydrogen at the same time is excluded.

2. The electrophotographic printing method according to feature 1, wherein the charge controlling agent contains a monoazo iron complex compound of the formula (2) as an effective component,

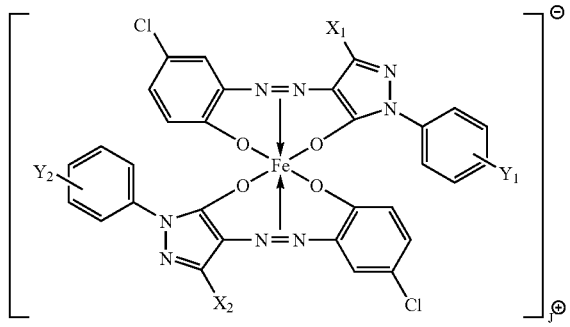

wherein J is H, Na, $NH_4$ or an alkylammonium, they may be two or more kinds (an alkyl group of the alkyl ammonium has a carbon number of 1 to 12, preferably 3 to 8, and a nitrogen atom may have 1 to 4 same or different alkyl groups bonded thereon), $X_1$ and $X_2$ are respectively independently H, an alkyl group or a halogen atom, and $Y_1$ and $Y_2$ are respectively independently H, an alkyl group or a halogen atom (the alkyl group has a carbon number of preferably 1 to 8, more preferably 1 to 4, and the halogen atom is preferably chlorine).

3. The electrophotographic printing method according to feature 1, wherein the charge controlling agent contains a monoazo iron complex compound of the formula (3) as an effective component,

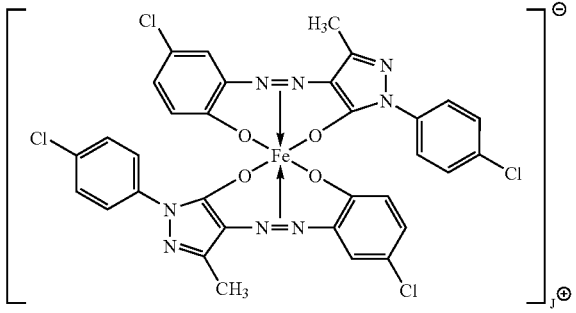

wherein J is H, Na, $NH_4$ or an alkylammonium, and they may be two or more kinds (an alkyl group of the alkyl ammonium has a carbon number of 1 to 12, preferably 3 to 8, and a nitrogen atom may have 1 to 4 same or different alkyl groups bonded thereon).

4. The electrophotographic printing method according to feature 1, wherein the charge controlling agent contains a monoazo iron complex compound of the formula (4) as an effective component,

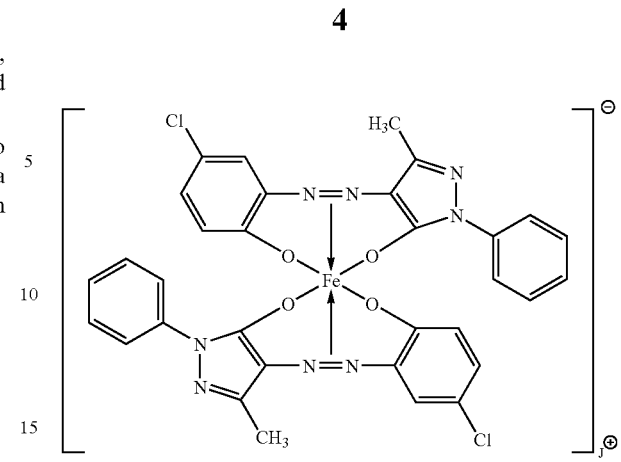

wherein J is H, Na, $NH_4$ or an alkylammonium, and they may be two or more kinds.

5. The electrophotographic printing method according to feature 1, wherein the charge controlling agent contains a monoazo iron complex compound of the formula (5) as an effective agent,

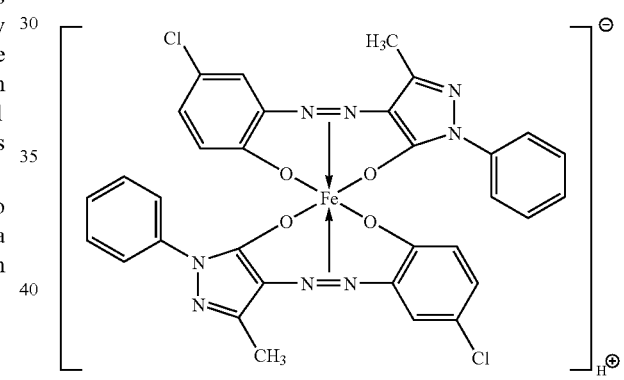

6. The electrophotographic printing method according to any one of features 1 to 5, wherein the charge controlling agent has a volume average particle size of from 0.1 to 20 μm.

7. A negatively chargeable toner which comprises a charge controlling agent as defined in any one of features 1 to 5, a coloring agent and a binder resin.

8. The toner according to feature 7, wherein the monoazo iron complex compound as an effective component of the charge controlling agent is incorporated within toner particles in an amount of from 0.1 to 10 mass parts per 100 mass parts of a binder resin.

9. The toner according to feature 7, wherein the monoazo iron complex compound as an effective component of the charge controlling agent is incorporated within toner particles in an amount of from 0.2 to 5 mass parts per 100 mass parts of a binder resin.

10. The toner according to any one of features 7 or 9, wherein the binder resin has an acid value of from 0.1 to 100 mgKOH/g.

11. The toner according to any one of features 7 to 10, wherein the coloring agent is a magnetic material.
12. The toner according to feature 11, wherein the magnetic material is magnetic iron oxide.
13. The toner according to feature 11 or 12, wherein the magnetic material is contained in an amount of 10 to 200 mass parts per 100 mass parts of a binder resin.
14. The toner according to any one of features 7 to 10, wherein the coloring agent is a non-magnetic coloring agent and is contained in an amount of from 0.1 to 20 mass parts per 100 mass parts of a binder resin.
15. The toner according to any one of features 7 to 14, wherein a wax is further contained.
16. The toner according to feature 15, wherein the wax has a melting point of 70° C. to 140° C.
17. The toner according to feature 15 or 16, wherein the wax is contained in an amount of 0.2 to 20 mass parts per 100 mass parts of a binder resin.
18. The toner according to any one of features 7 to 17, wherein the toner has a volume average particle size of from 2 to 15 μm.
19. The toner according to any one of features 7 to 17, wherein the toner has a volume average particle size of from 3 to 12 μm.
20. A one-component system developer which comprises the negatively chargeable toner as defined in any one of features 7 to 19.
21. A two-component system developer which comprises a negatively chargeable toner and a carrier, wherein the toner contains at least a binder resin, a coloring agent and a monoazo iron complex compound, and the monoazo iron complex compound is a monoazo iron complex compound as an effective component of the charge controlling agent as defined in any one of features 1 to 5.
22. The two-component system developer according to feature 21, wherein the monoazo iron complex compound is incorporated within toner particles in an amount of from 0.1 to 10 mass parts per 100 mass part of the binder resin.
23. The two-component system developer according to feature 21, wherein the monoazo iron complex compound is incorporated within toner particles in an amount of from 0.2 to 5 mass parts per 100 mass part of the binder resin.
24. The two-component system developer according to any one of features 21 to 23, wherein the toner contains a styrene-acryl type resin as a binder resin.
25. The two-component system developer according to feature 24, wherein the binder resin has an acid value of from 0.1 to 100 mgKOH/g.
26. The two-component system developer according to feature 24, wherein the binder resin has an acid value of from 0.1 to 50 mgKOH/g
27. The two-component system developer according to any one of features 21 to 26, wherein the binder resin has a glass transition temperature (Tg) of 35 to 80° C.
28. The two-component system developer according to any one of features 21 to 27, wherein a wax is further contained.
29. The toner according to feature 28, wherein the wax has a melting point of 70° C. to 140° C.
30. The toner according to feature 28 or 29, wherein the wax is contained in an amount of 0.2 to 20 mass parts by 100 mass parts of a binder resin.
31. The two-component system developer according to any one of features 21 to 30, wherein the toner has a volume average particle size of from 2 to 15 μm.
32. The two-component system developer according to any one of features 21 to 30, wherein the toner has a volume average particle size of from 3 to 12 μm.
33. The two-component system developer according to any one of features 21 to 32, wherein the carrier is a resin-coated carrier.
34. The two-component system developer according to feature 33, wherein the resin-coated carrier comprises carrier core particles and a coating resin coating a surface of the carrier core particles, the coating resin being at least one resin selected from the group consisting of polytetrafluoroethylene, monochlorotrifluoroethylene polymer, polyvinylidene fluoride, silicone resin, polyester, styrenic resin, acrylic resin, polyamide, polyvinyl butyral and aminoacrylate resin.
35. A monoazo iron complex compound of the formula (3),

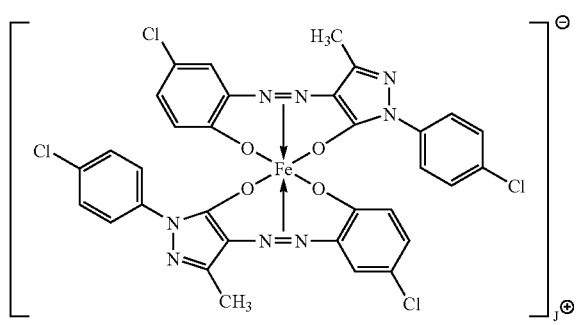

wherein J is H, Na, $NH_4$ or an alkylammonium, and they may be two or more kinds.
36. A monoazo iron complex compound of the formula (4),

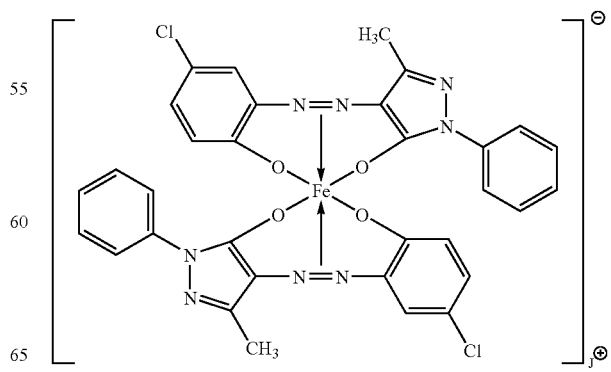

wherein J is H, Na, NH$_4$ or an alkylammonium, and they may be two or more kinds.

37. A monoazo iron complex compound of the formula (5),

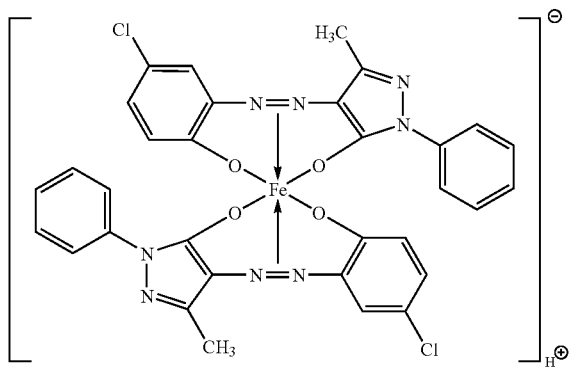

DETAILED DESCRIPTION OF THE PREFERRED EMBODIMENTS

Figure 1:
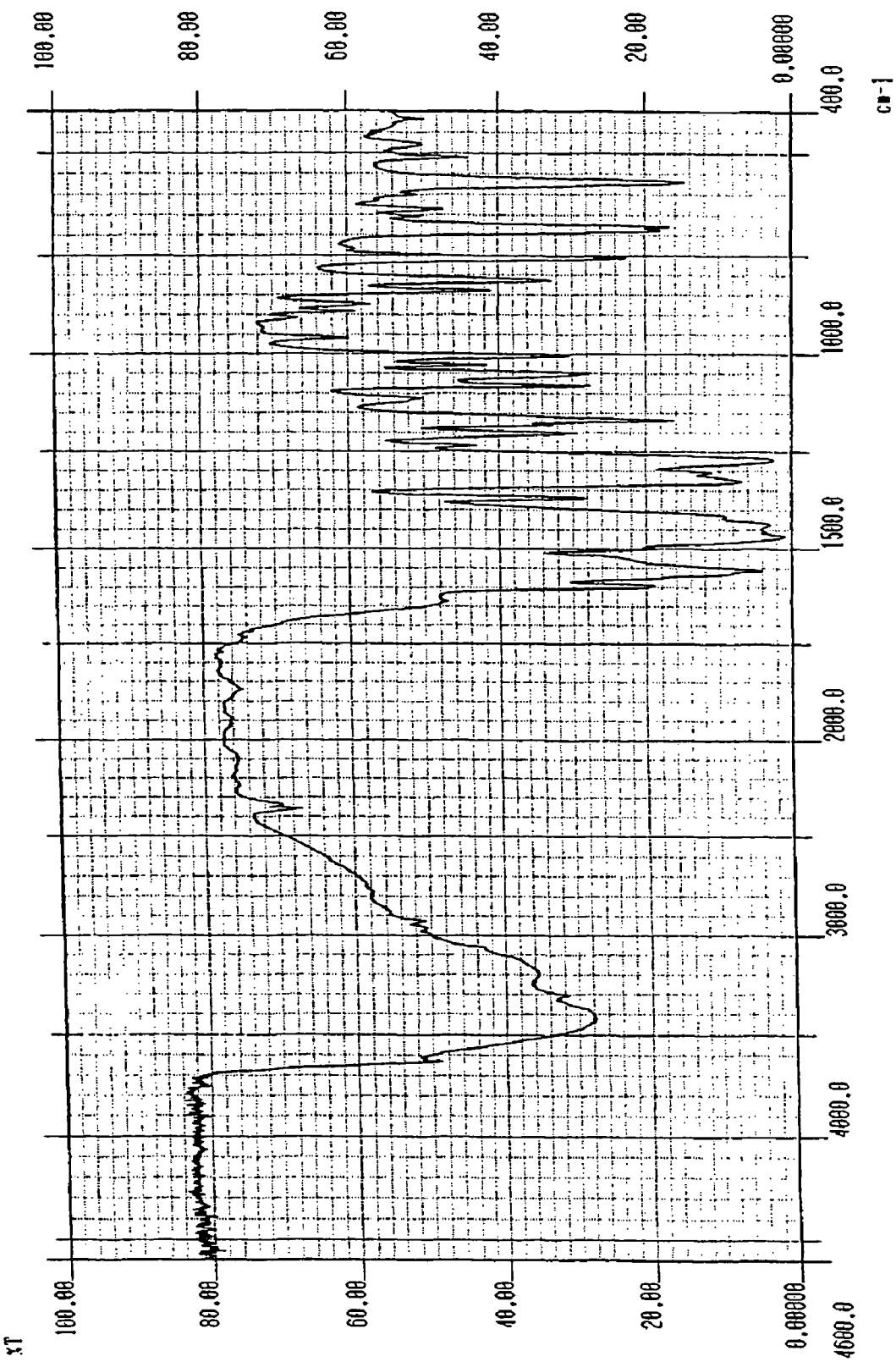
FIG. 1 illustrates an infrared ray-absorption spectrum chart of compound No. 1 in Table 1 of the present invention.
Figure 2:
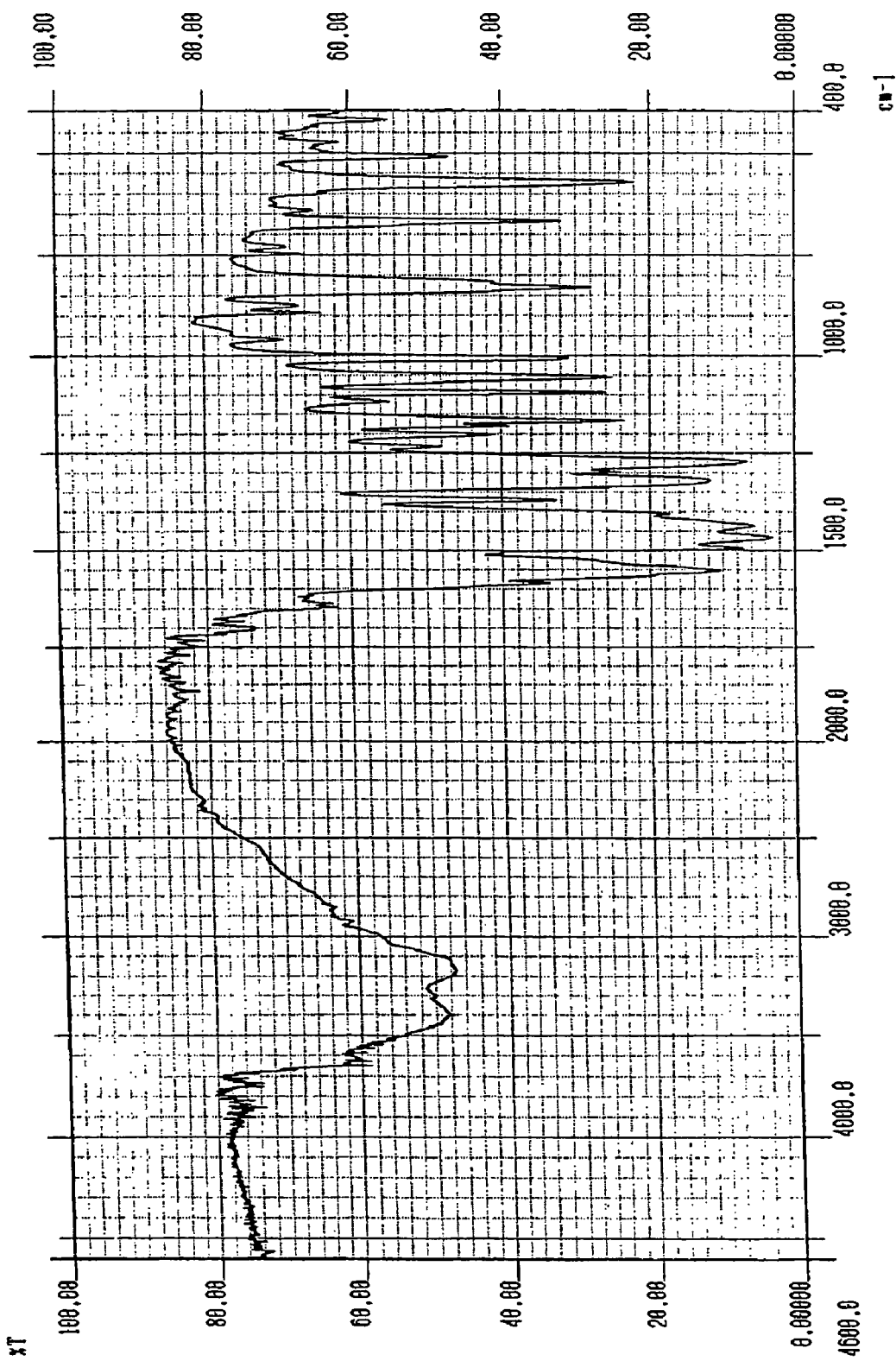
FIG. 2 illustrates an infrared ray-absorption spectrum chart of compound No. 2 in Table 1 of the present invention.
Figure 3:
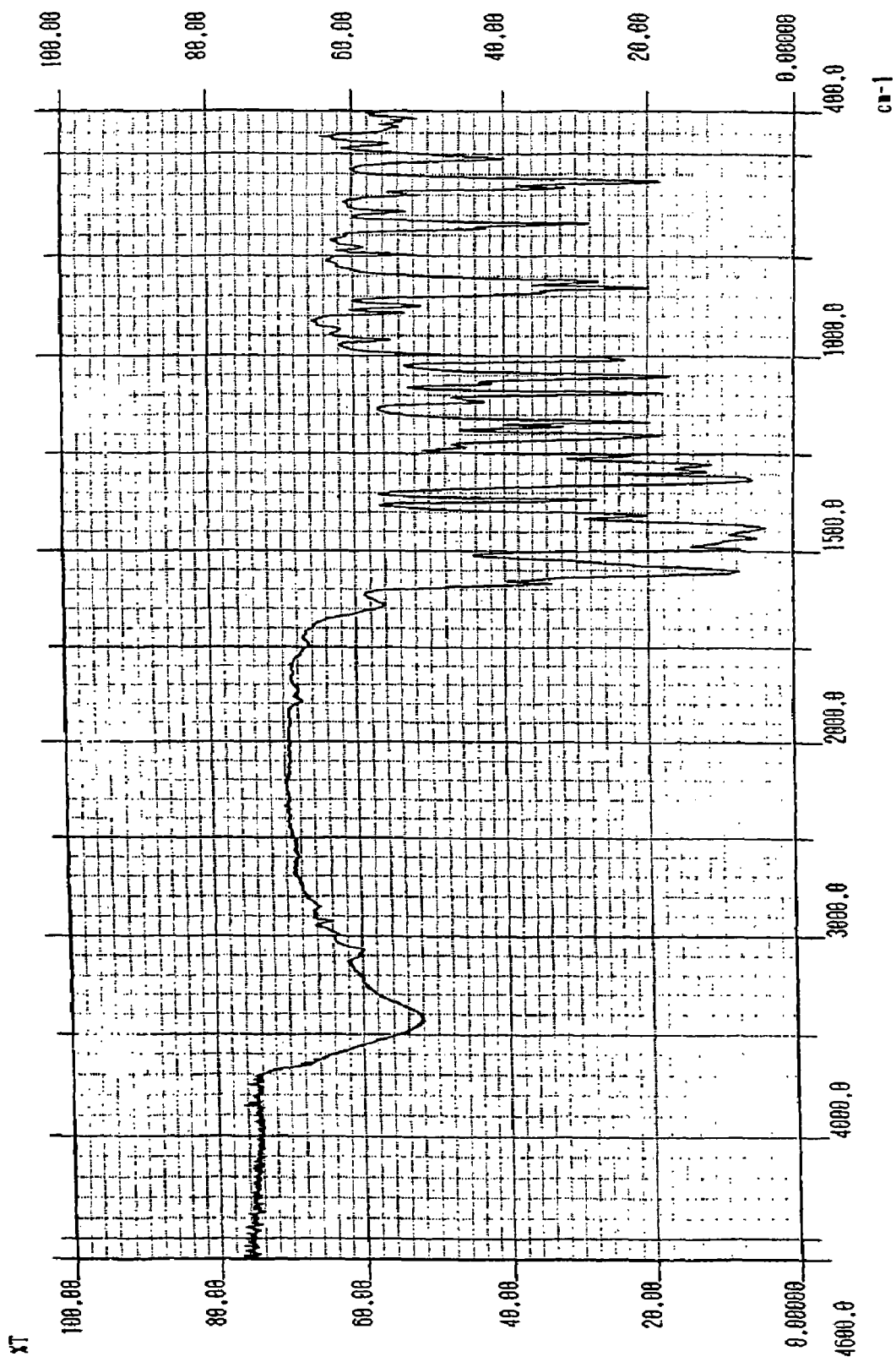
FIG. 3 illustrates an infrared ray-absorption spectrum chart of compound No. 3 in Table 1 of the present invention.
Figure 4:
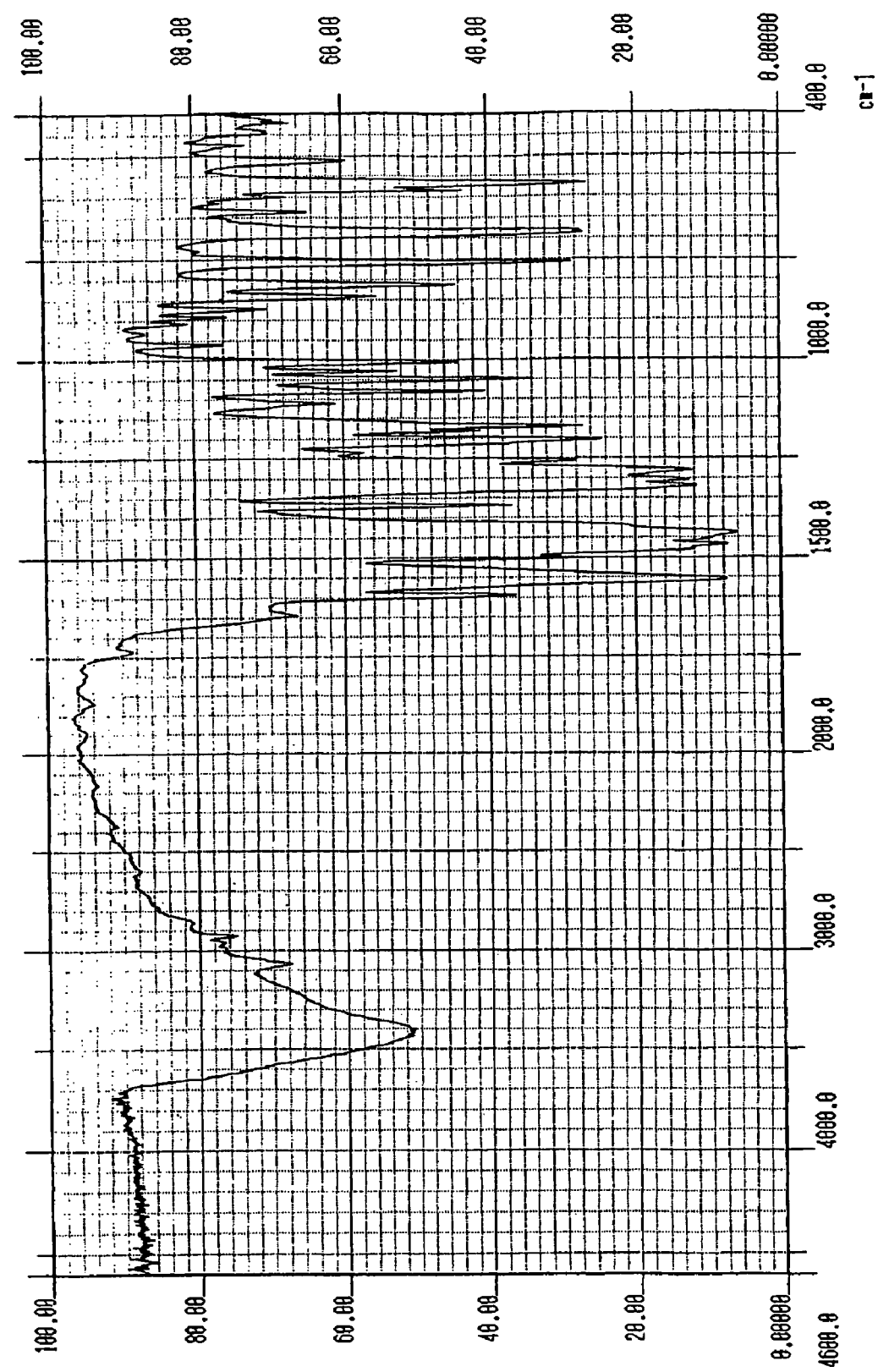
FIG. 4 illustrates an infrared ray-absorption spectrum chart of compound No. 4 in Table 1 of the present invention.
Figure 5:
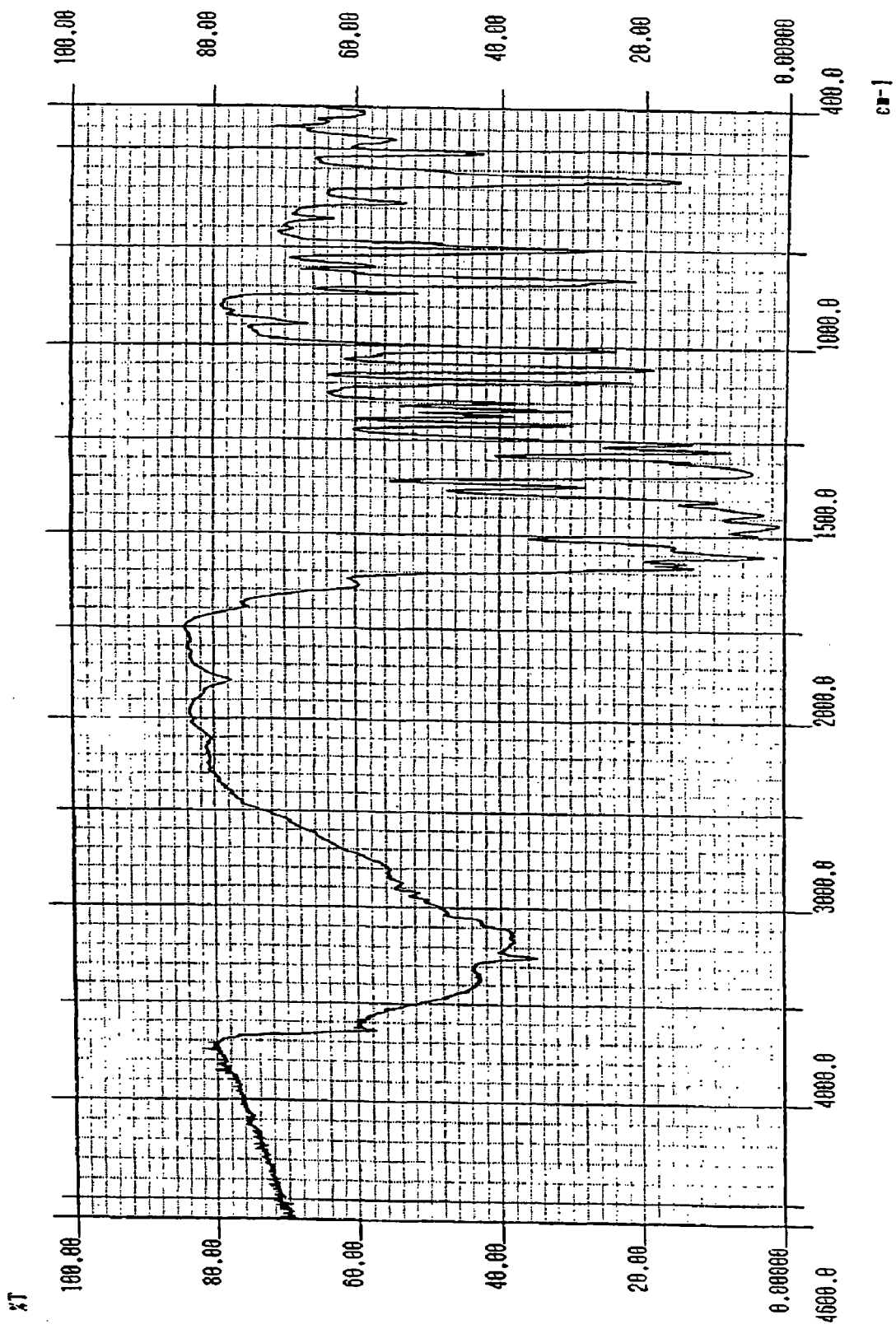
FIG. 5 illustrates an infrared ray-absorption spectrum chart of compound No. 5 in Table 1 of the present invention.
Figure 6:
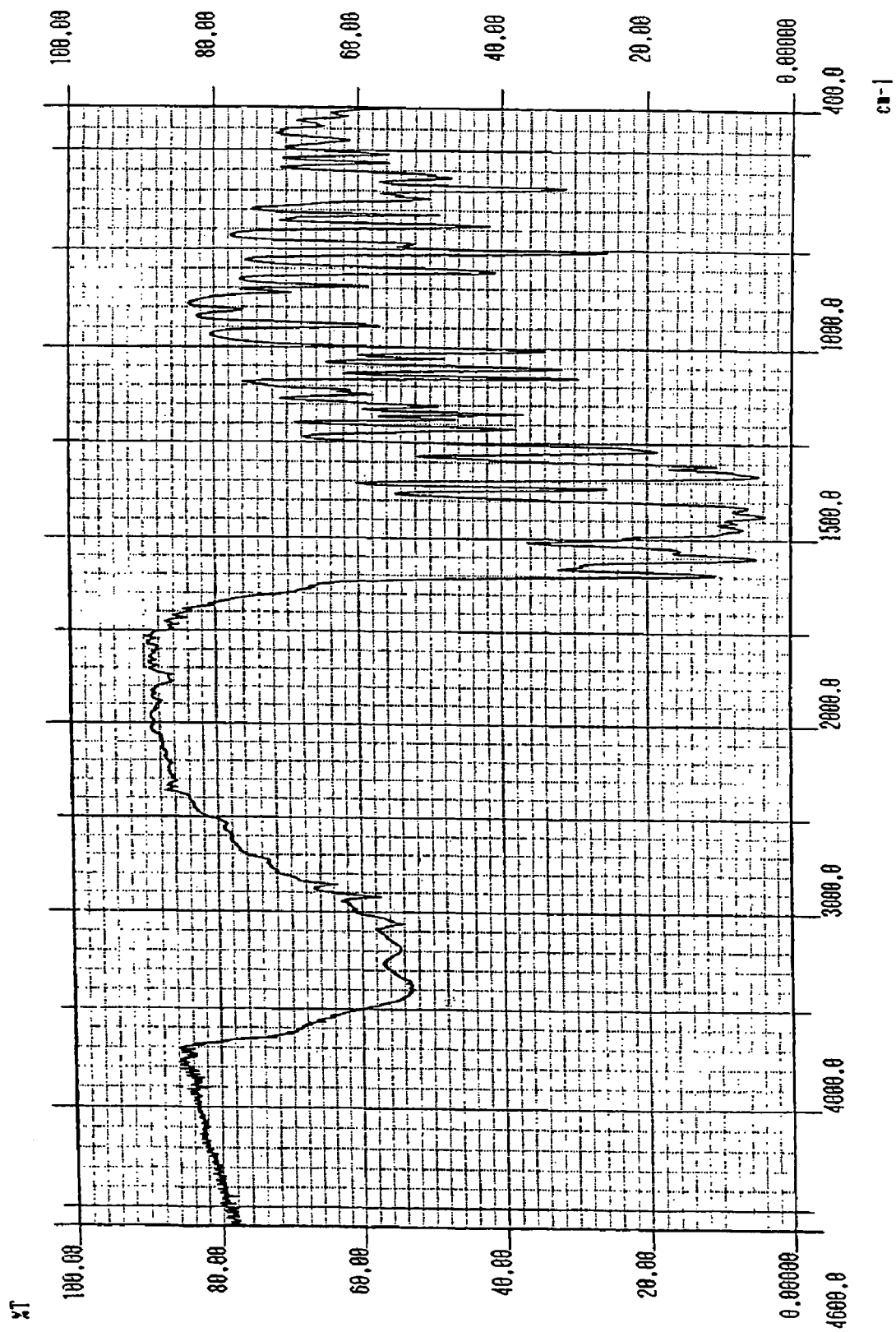
FIG. 6 illustrates an infrared ray-absorption spectrum chart of compound No. 6 in Table 1 of the present invention.
Figure 7:
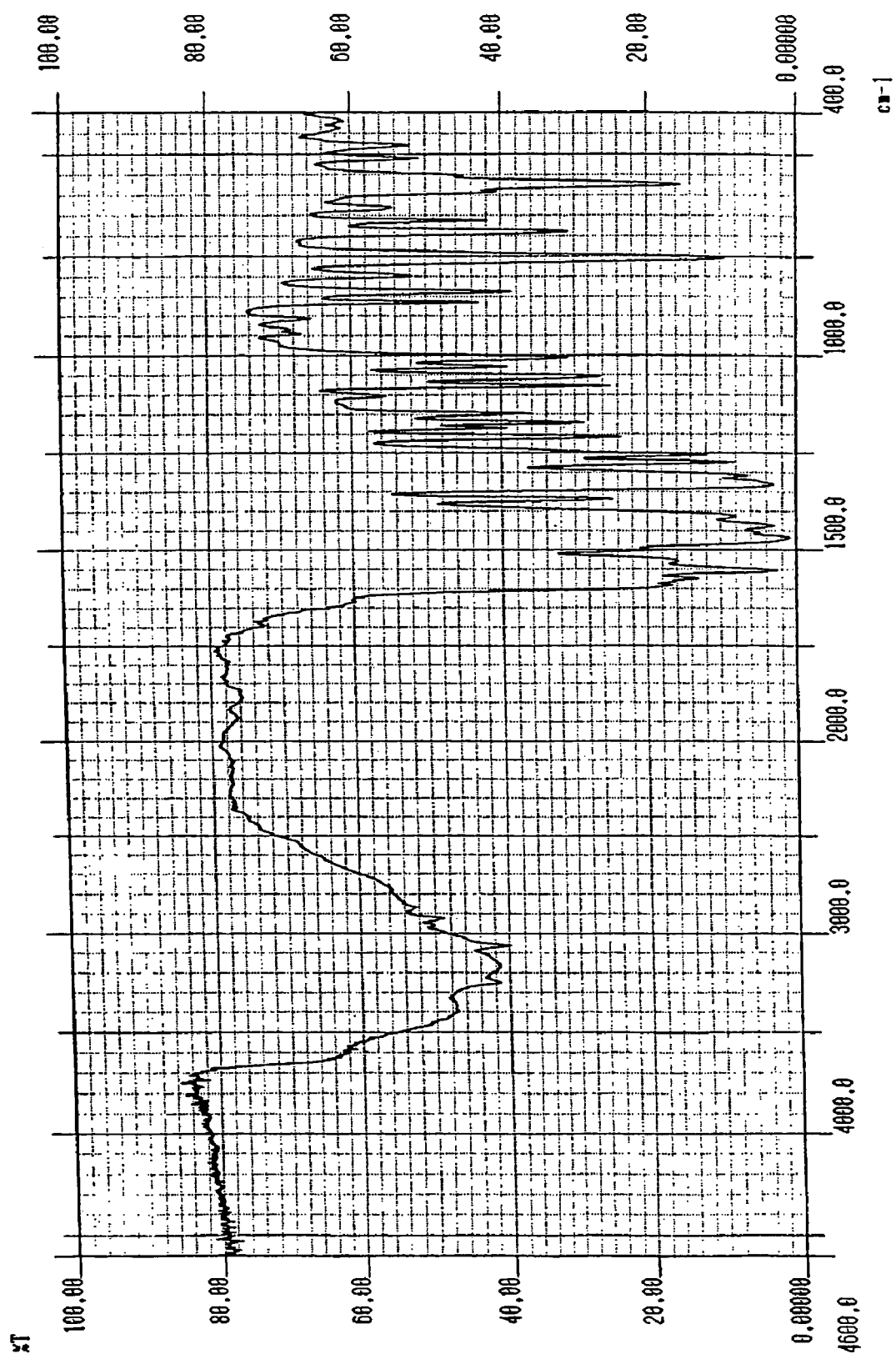
FIG. 7 illustrates an infrared ray-absorption spectrum chart of compound No. 11 in Table 1 of the present invention.
Figure 8:
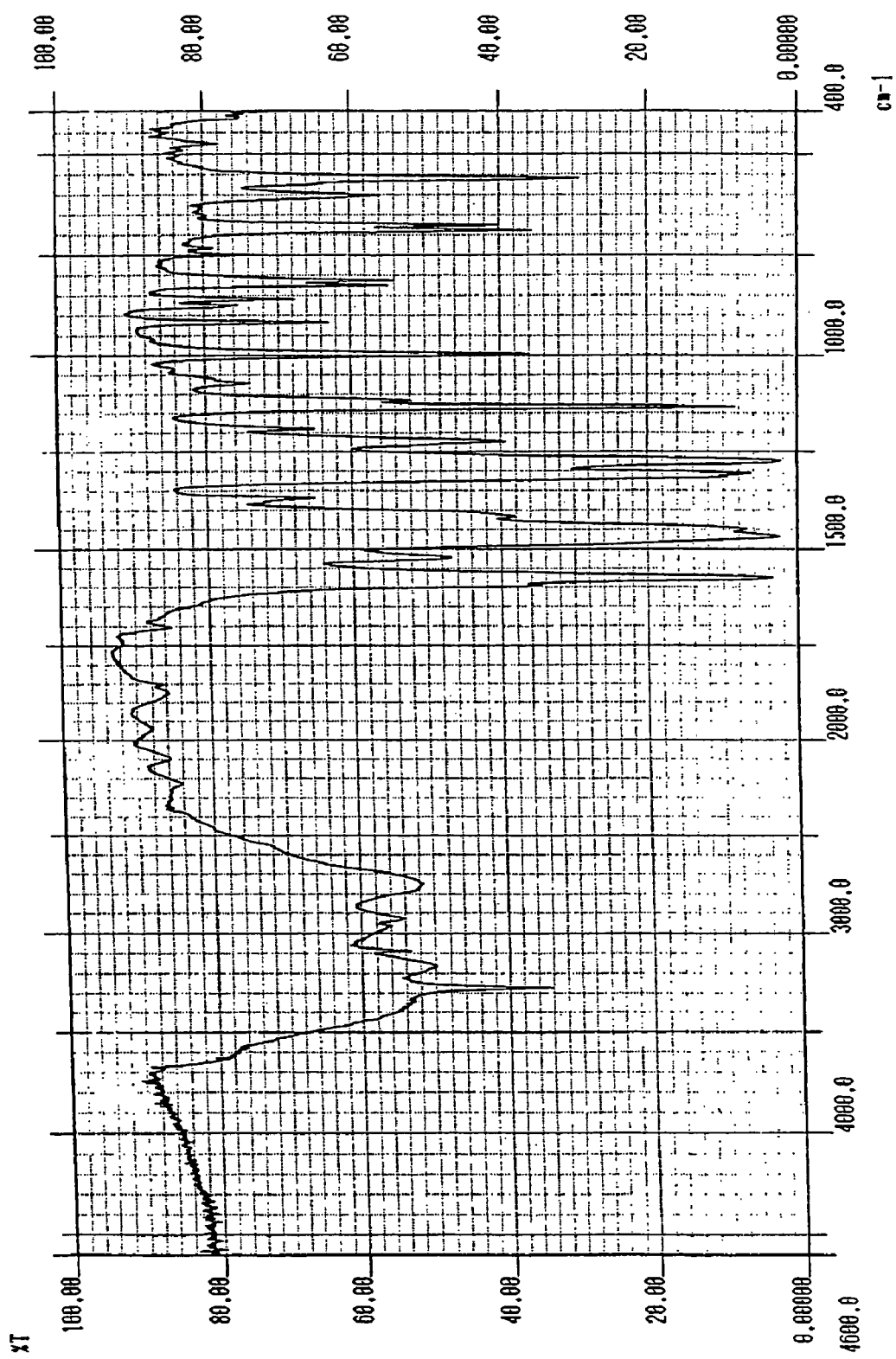
FIG. 8 illustrates an infrared ray-absorption spectrum chart of compound No. 12 in Table 2 of the present invention.
Figure 9:
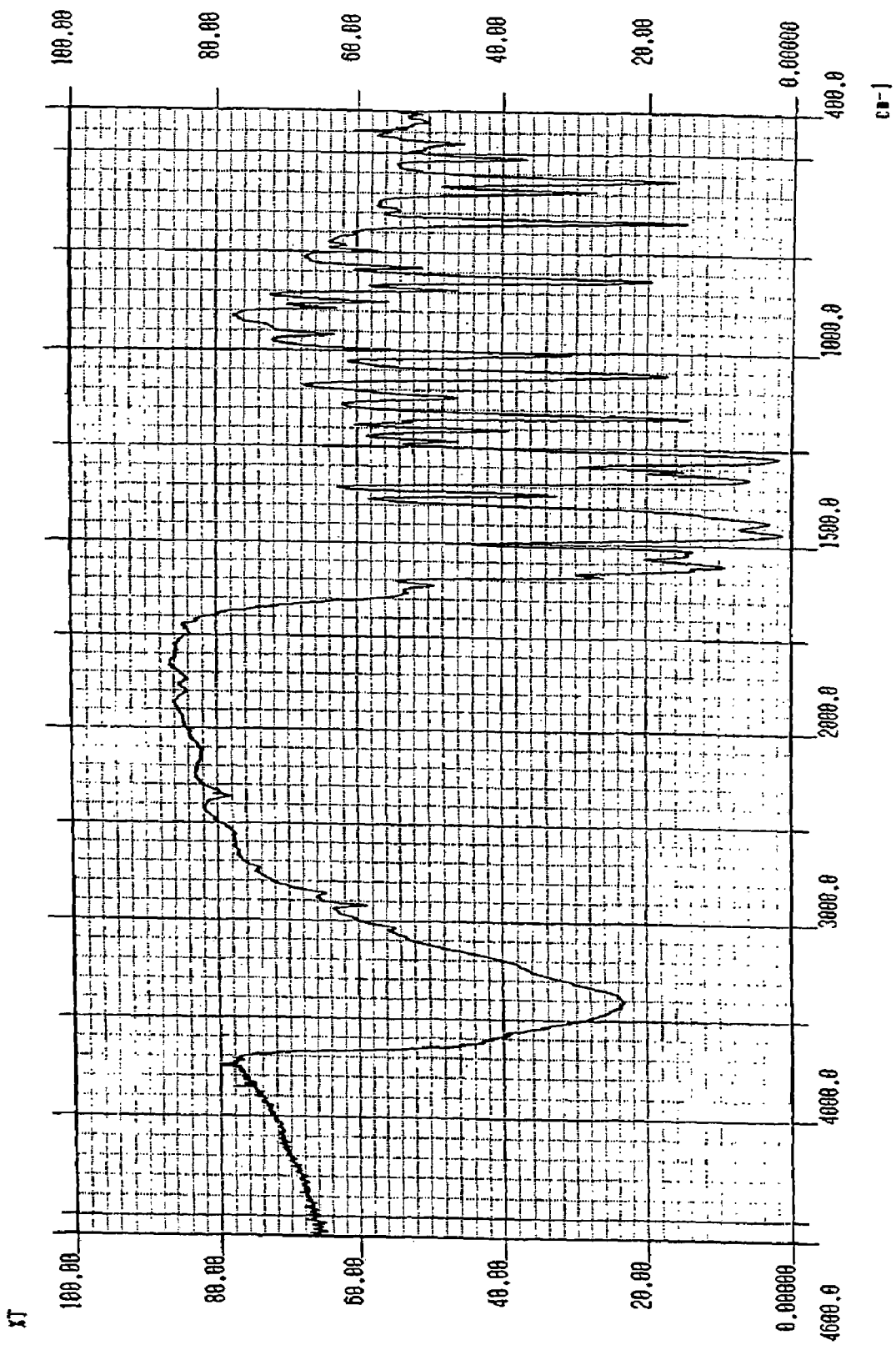
FIG. 9 illustrates an infrared ray-absorption spectrum chart of compound No. 13 in Table 2 of the present invention.
Figure 10:
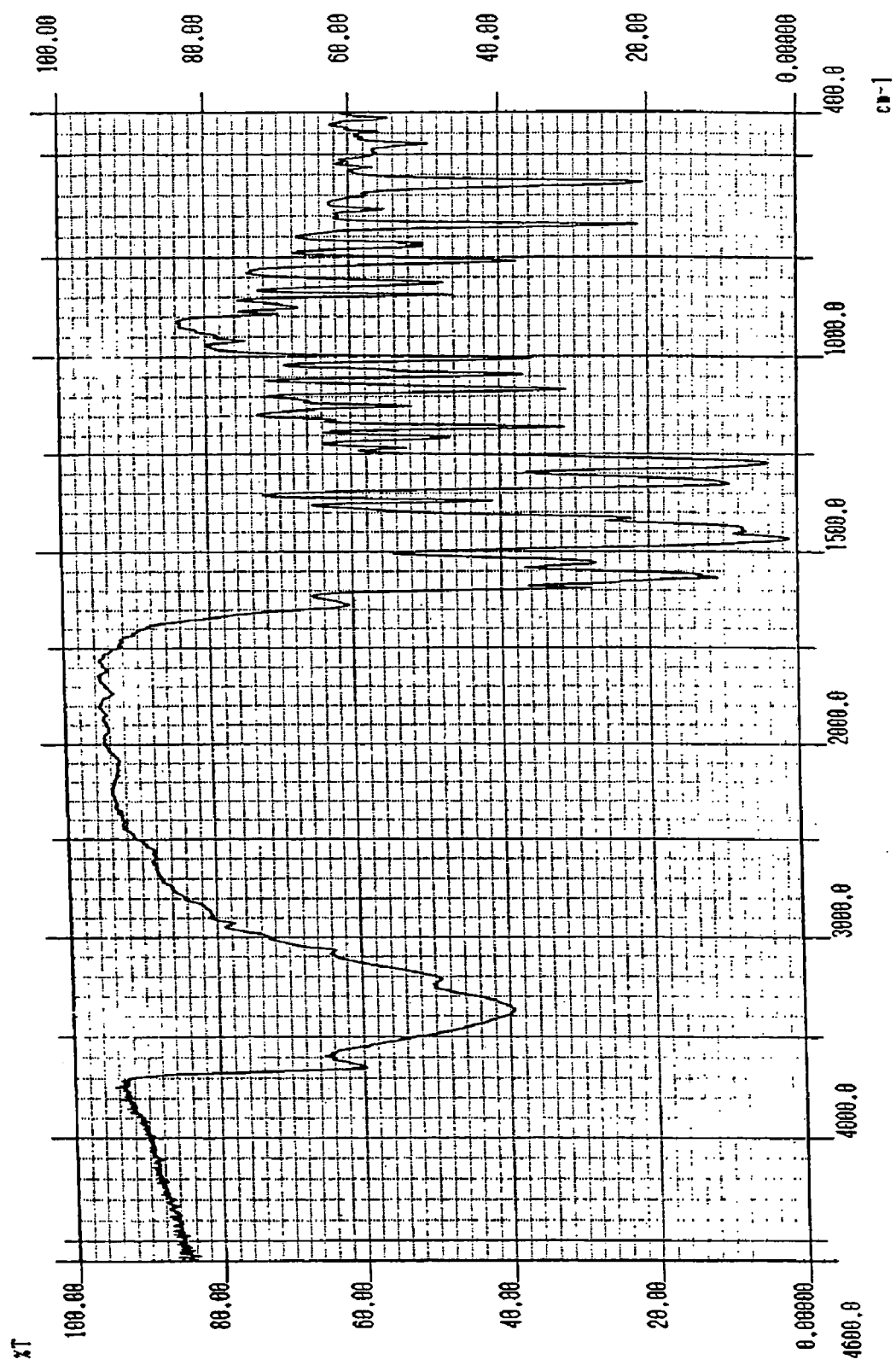
FIG. 10 illustrates an infrared ray-absorption spectrum chart of compound No. 14 in Table 2 of the present invention.
Figure 11:
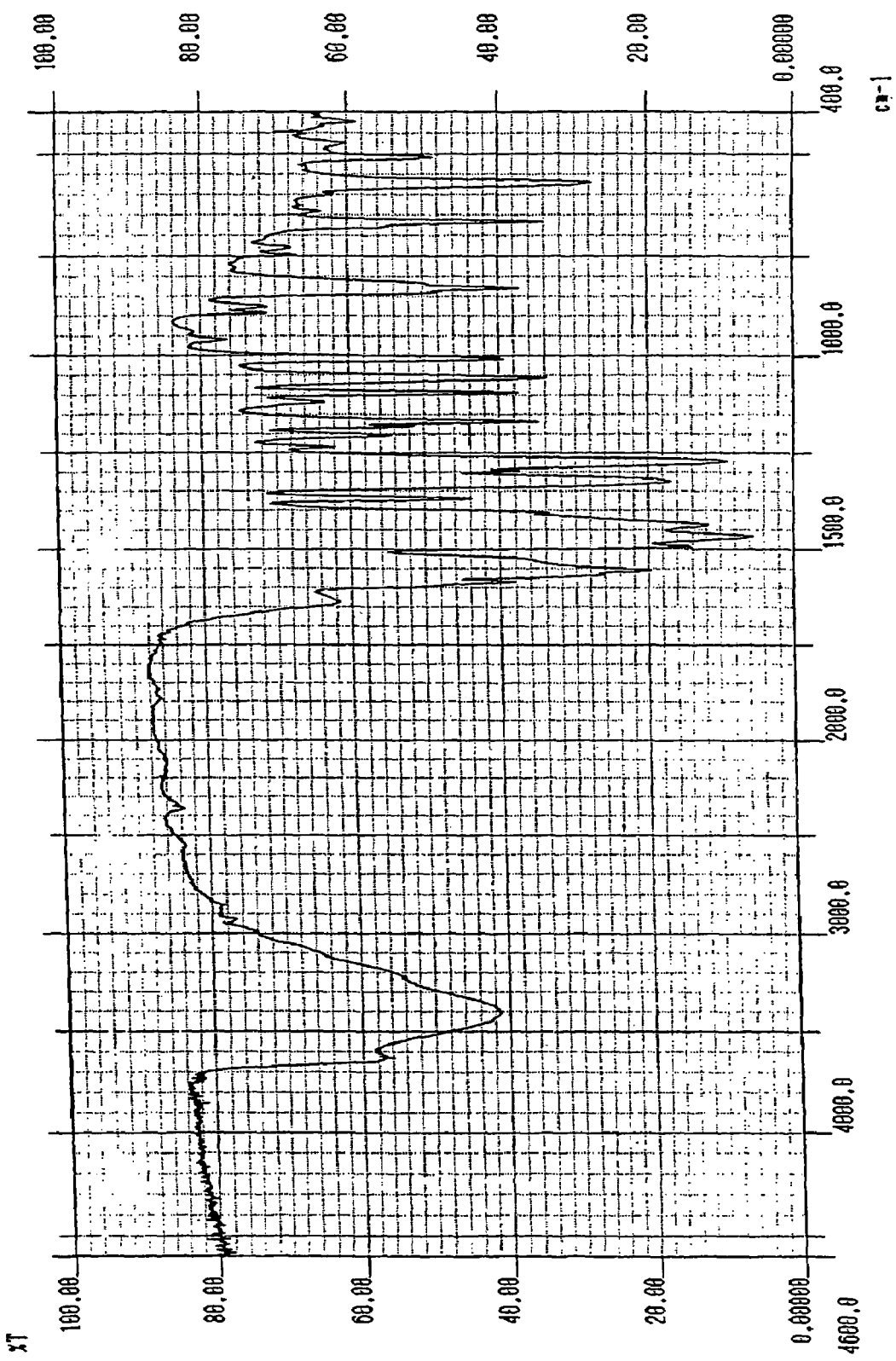
FIG. 11 illustrates an infrared ray-absorption spectrum chart of compound No. 15 in Table 2 of the present invention.
Figure 12:
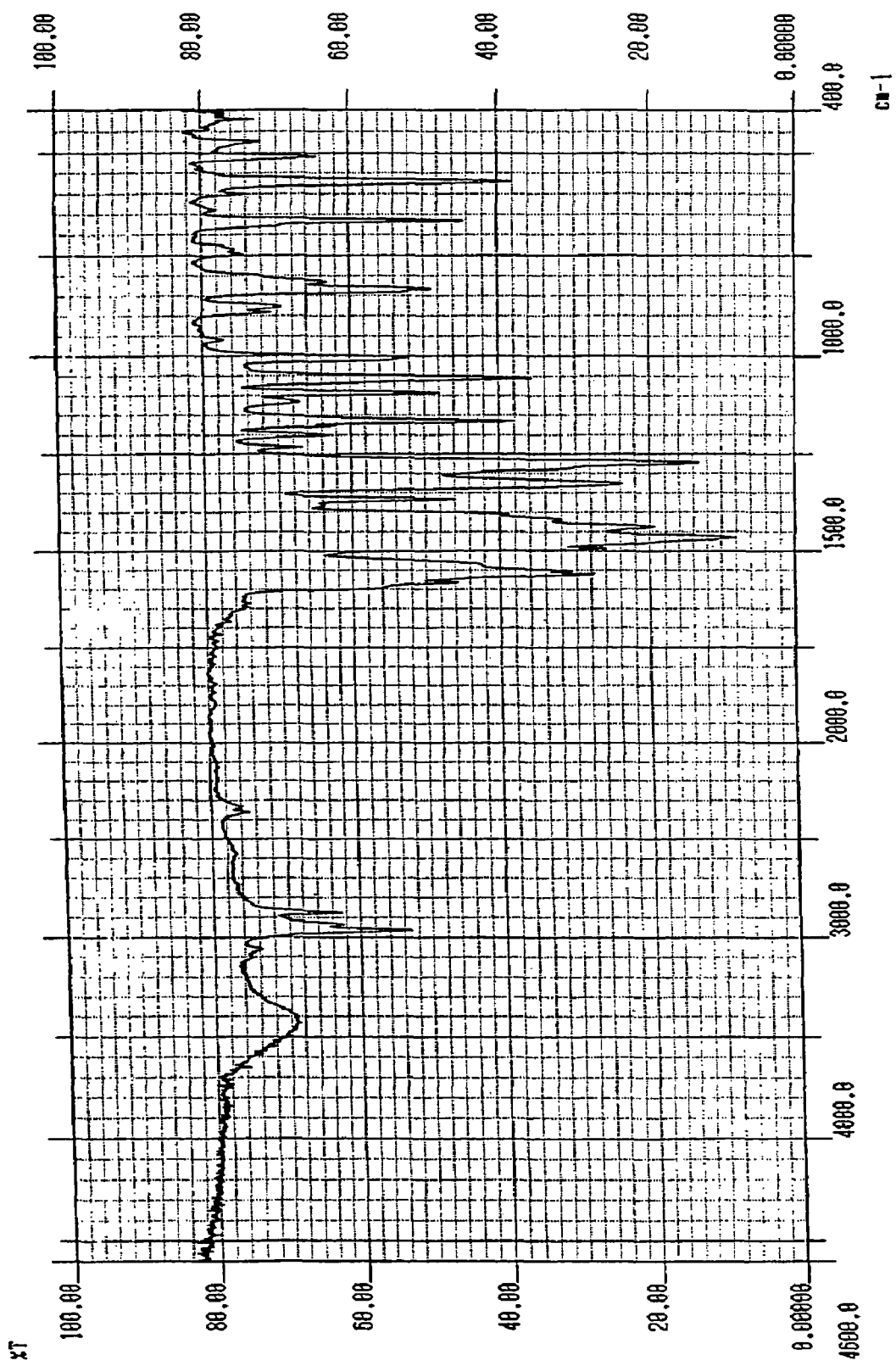
FIG. 12 illustrates an infrared ray-absorption spectrum chart of compound No. 19 in Table 2 of the present invention.
Figure 13:
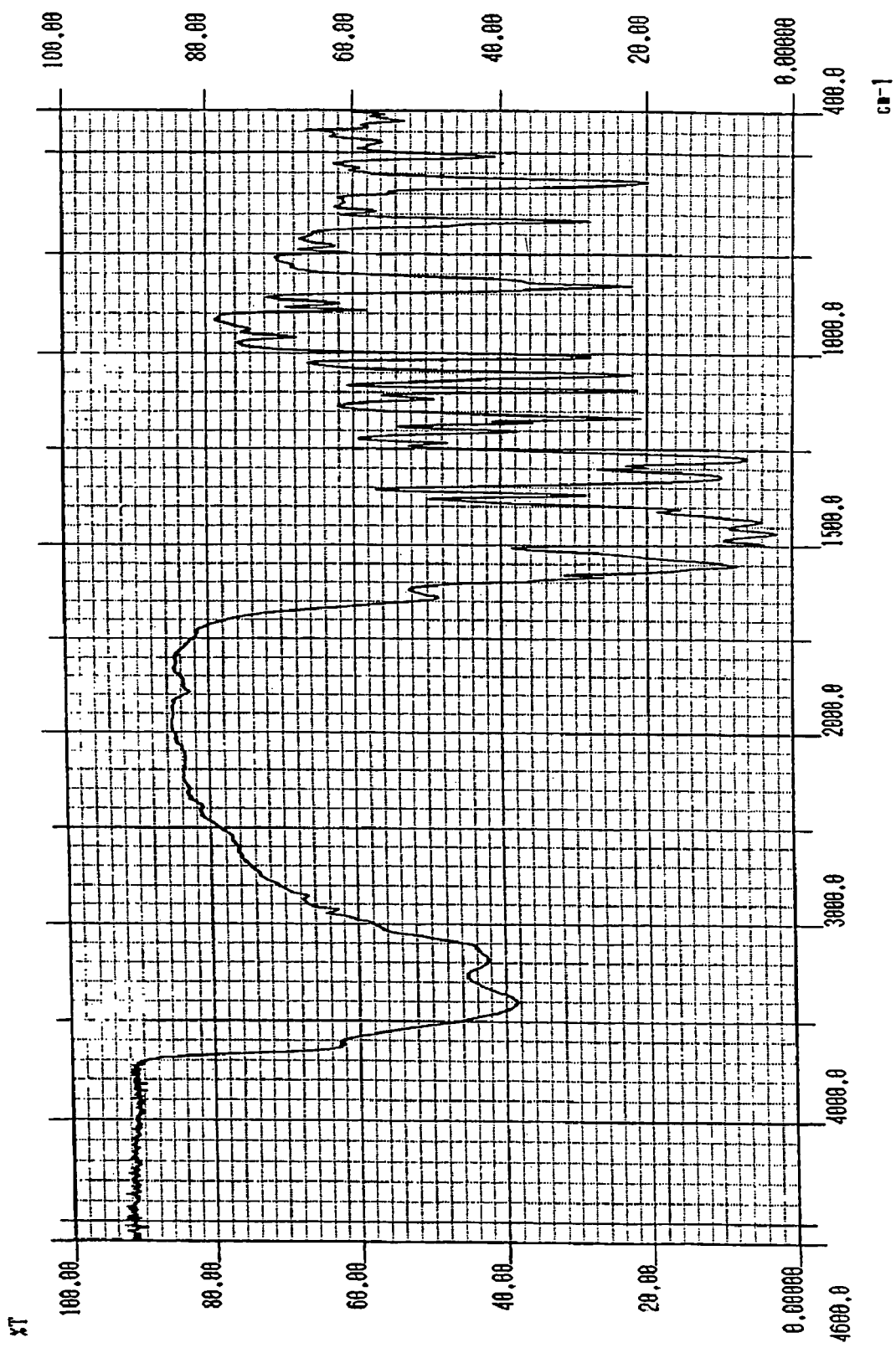
FIG. 13 illustrates an infrared ray-absorption spectrum chart of compound No. 21 in Table 2 of the present invention.
Figure 14:
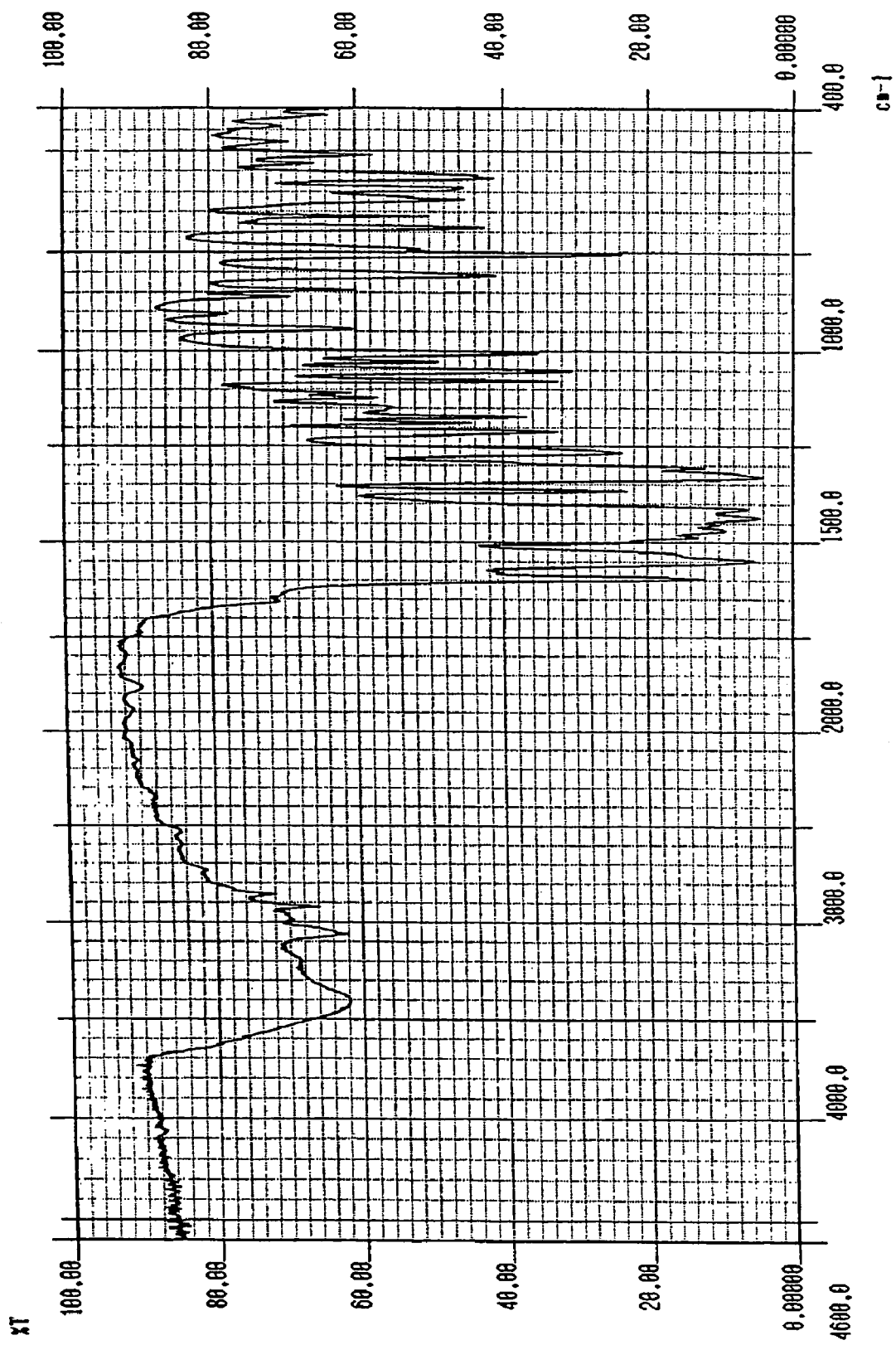
FIG. 14 illustrates an infrared ray-absorption spectrum chart of compound No. 22 in Table 2 of the present invention.

The charge controlling agent of the present invention has a remarkably satisfactory quick chargeability, and the toner can be charged in a shorter time as compared with a conventional charge controlling agent. Also, with regard to a charged amount, the charge controlling agent of the present invention has an effect of achieving a high chargeability, and the charged amount is stable to surrounding temperature, humidity or the like and to environmental changes. Further, the compound has a high safety since it does not contain such an environmentally noxious metal as chromium and does not have such a substituent as a nitro group highly ignitable.

The toner containing the charge controlling agent of the present invention provides an excellent image highly evaluated in respect of image properties such as image density, fog density, dot reproducibility or thin line reproducibility regardless of one component- or two component-developing system.

The monoazo iron complex compound of the present invention is a compound excellent in environmental stability and also excellent in charge controlling effect. A toner containing the monoazo iron complex compound of the present invention achieves a quick chargeability and a high charged amount, and consequently provides a clear sharp image.

The monoazo iron complex compound of the present invention can be produced by a well known method for producing a monoazo complex compound, and a typical production method is illustrated below but should not be limited thereto. First, a mineral acid such as hydrochloric acid or sulfuric acid is added to a diazo component such as 4-chloro-2-aminophenol, and when an internal temperature is lowered to 5° C. or lower, sodium nitrite dissolved in water is dropwise added thereto while maintaining the internal temperature at 10° C. or lower. The resultant mixture is reacted by stirring at 10° C. or lower for 30 minutes to 3 hours to diazotize 4-chloro-2-aminophenol. By adding sulfamic acid, it is confirmed by potassium iodide starch paper that the nitrous acid does not remain in an excess amount.

Thereafter, a coupling component such as 3-methyl-1-(4-chlorophenyl)-5-pyrazolone or the like, a sodium hydroxide aqueous solution, sodium carbonate and an organic solvent such as butanol or the like are added, and the resultant mixture is dissolved by stirring at room temperature. The above obtained diazotized compound is added thereto, and the resultant mixture is stirred at room temperature for a few hours to carry out coupling reaction. After stirring, the reaction is finished by confirming that there is no further reaction of the diazotized compound and resorcin. After adding water, the mixture is fully stirred, and is allowed to stand for separating the solution. A sodium hydroxide aqueous solution is further added thereto, and the mixture is subjected to stirring and washing to separate the solution.

Examples of an organic solvent other than butanol usable for the above coupling reaction include any solvent usable for coupling, preferably a monohydric alcohol or a dihydric alcohol. Examples of the monohydric alcohol include methanol, ethanol, n-propanol, 2-propanol, n-butanol, isobutanol, sec-butanol, n-amyl alcohol, isoamyl alcohol, ethylene glycol monoalkyl ether (having a carbon number of from 1 to 4) and the like. Examples of the dihydric alcohol include ethylene glycol and the like. Among them, butanol is preferable as a solvent.

A butanol solution of the above monoazo compound is stirred after adding water, salicylic acid, n-butanol and sodium carbonate thereto. A ferric chloride aqueous solution and sodium carbonate are further added thereto. An inner temperature is raised to 30 to 40° C., and the reaction is analyzed by TLC. After 5 to 10 hours, the reaction is finished by confirming that a spot of starting material disappears. After stirring, the reaction mixture is allowed to stand to separate the solution. Water, butanol and a sodium hydroxide aqueous solution are further added thereto, and the resultant solution is subjected to alkali washing. The solution is filtrated to recover a cake which is then washed with water.

Ammonium sulfate is added to water and is stirred while raising an internal temperature. When the internal temperature is raised to 85 to 90° C., a dispersion solution of the above obtained cake is dropwise added thereto. The resultant mixture is stirred for 1 hour while distilling off butanol at 97° C. to 99° C., and is cooled and filtrated to obtain a cake which is then washed with water. After drying the resultant product under vacuum and confirming that the product reaches a constant rate, a monoazo iron complex compound of the present invention can be obtained.

Concrete examples of the monoazo iron complex compound of the present invention thus obtained are illustrated in the following Tables 1 and 2, but the compounds of the present invention are not limited thereto. In the following Tables 1 and 2, marks $A_1$, $A_2$, $B_1$, $B_2$, J, $X_1$, $X_2$, $Y_1$ and $Y_2$ are respectively the same as defined in the above formula (1), and bonded parts in the Tables respectively correspond to figures of substituted positions as defined in the above formula (1). Also, "Bu" and "Pr" of pair ion J of compounds No. 19 and No. 20 in Table 2 indicate respectively "normal butyl group" and "normal propyl group", and pair ion J of compound No. 21 comprises 90% of $NH_4$, 5% of Na and 5% of H.

TABLE 1

| | | Structure of Compound | | | | | |
|---|---|---|---|---|---|---|---|
| | $A_1, A_2$ | | $B_1, B_2$ | | | | |
| Comp. No. | Bonded part | Substituent | Bonded part | Substituent | J | $X_1, X_2$ | $Y_1, Y_2$ |
| 1 | — | —H | 4 | —Cl | $NH_4$ | —$CH_3$ | 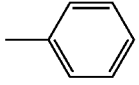 |
| 2 | — | —H | 4 | —Cl | $NH_4$ | —$CH_3$ |  |
| 3 | — | —H | 4 | —Cl | H | —$CH_3$ | 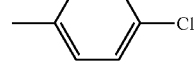 |
| 4 | — | —H | 4 | —Cl | H | —$CH_3$ | 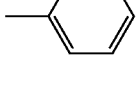 |
| 5 | — | —H | — | —H | $NH_4$ | —$CH_3$ | 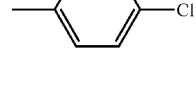 |
| 6 | — | —H | 4 | —$CH_3$ | $NH_4$ | —$CH_3$ | 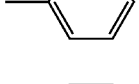 |
| 7 | 5 | —$CH_3$ | 4 | —Cl | $NH_4$ | —$CH_3$ | 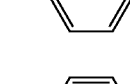 |
| 8 | 5 | —$CH_3$ | — | —H | $NH_4$ | —$CH_3$ | 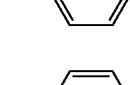 |
| 9 | 5 | —Cl | 4 | —Cl | $NH_4$ | —$CH_3$ | 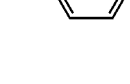 |

TABLE 1-continued

Structure of Compound

| Comp. No. | A₁, A₂ Bonded part | A₁, A₂ Substituent | B₁, B₂ Bonded part | B₁, B₂ Substituent | J | X₁, X₂ | Y₁, Y₂ |
|---|---|---|---|---|---|---|---|
| 10 | 6 | —Cl | 4 | —Cl | $NH_4$ | —CH₃ | 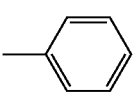 |
| 11 | — | —H | — | —H | $NH_4$ | —CH₃ | 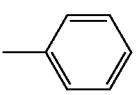 |

TABLE 2

Structure of Compound

| Comp. No. | A₁, A₂ Bonded part | A₁, A₂ Substituent | B₁, B₂ Bonded part | B₁, B₂ Substituent | J | X₁, X₂ | Y₁, Y₂ |
|---|---|---|---|---|---|---|---|
| 12 | — | —H | 4 | —Cl | $NH_4$ | —CH₃ | —CH'₃ |
| 13 | — | —H | 4 | —Cl | $NH_4$ | —CH₃ | 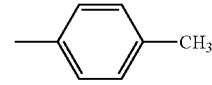 |
| 14 | — | —H | 4 | —Cl | $NH_4$ | —CH₃ | 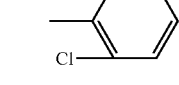 |
| 15 | — | —H | 4 | —Cl | Na | —CH₃ | 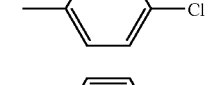 |
| 16 | — | —H | 4 | —Cl | K | —CH₃ | 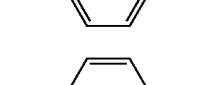 |
| 17 | — | —H | 4 | —Cl | Li | —CH₃ | 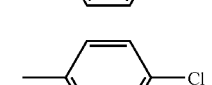 |
| 18 | — | —H | 4 | —Cl | (t-Bu)₄N | —CH₃ | 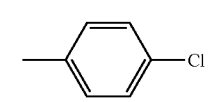 |
| 19 | — | —H | 4 | —Cl | (Bu)₄N | —CH₃ | 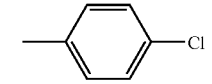 |
| 20 | — | —H | 4 | —Cl | (Pr)₄N | —CH₃ |  |

TABLE 2-continued

| | Structure of Compound | | | | | | |
|---|---|---|---|---|---|---|---|
| | $A_1, A_2$ | | $B_1, B_2$ | | | | |
| Comp. No. | Bonded part | Substituent | Bonded part | Substituent | J | $X_1, X_2$ | $Y_1, Y_2$ |
| 21 | — | —H | 4 | —Cl | $NH_4$, Na, H | —$CH_3$ | —⟨phenyl⟩—Cl |
| 22 | 5 | —$CH_3$ | — | —H | H | —$CH_3$ | —⟨phenyl⟩ |

The charge controlling agent of the present invention is a monoazo iron complex compound expressed by the above formula (1), preferably the above formula (2), more preferably the above formula (4), most preferably the above formulae (3) and (5), and may be one or a combination of two or more monoazo iron complex compounds expressed by the above formulae (1) to (5). Also, an unreacted starting material or intermediate, or a reaction accelerator such as salicylic acid, may be contained in an amount of at most 10%.

The charge controlling agent of the present invention is excellent in a charge controlling property, an environmental resistance and a durability, and a toner containing the charge controlling agent of the present invention produces no fog, and provides an image satisfactory in respect of an image density, a dot reproducibility and a thin line reproducibility.

The toner containing the monoazo iron complex compound of the present invention provides a stable developing performance without varying a chargeability even under high humidity or low humidity environments.

The charge controlling agent of the present invention is used by adjusting a volume average particle size to preferably from 0.1 to 20 μm, more preferably from 0.1 to 10 μm. If the above volume average particle size is smaller than 0.1 μm, an amount of the charge controlling agent appeared on the toner surface is too small to achieve an aimed charge controlling effect, and if the above volume average particle size is larger than 20 μm, an amount of the charge controlling agent dropped from the toner increases and produces a bad influence such as contamination in a copying machine.

Examples of a method for having a monoazo iron complex compound as a charge controlling agent incorporated into a toner used in the present invention include a method which comprises adding a monoazo iron complex compound to a binder resin together with a colorant, kneading the resultant mixture and pulverizing the kneaded mixture (pulverized toner), a method which comprises adding a monoazo iron complex compound to a polymerizable monomer and polymerizing the mixture to obtain a toner (polymerized toner), i.e. a method of previously adding the monoazo iron complex compound to the inside of toner particles (adding to the inside), and a method which comprises previously preparing toner particles and adding a monoazo iron complex compound to the surface of toner particles (adding to the outside). An amount of the monoazo iron complex compound of the present invention to be added to the inside of toner particles is preferably from 0.1 to 10 mass parts, more preferably from 0.2 to 5 mass parts, to 100 mass parts of a binder resin. Also, an amount of the monoazo iron complex compound of the present invention to be added to the outside of toner particles is preferably from 0.01 to 5 mass parts, more preferably from 0.01 to 2 mass parts, to 100 parts of a binder resin. It is preferable that the monoazo iron complex compound is mechanochemically fixed on the surface of toner particles.

Further, a charge controlling agent using the monoazo iron complex compound of the present invention as an effective component may be used in combination with well known other negatively chargeable charge controlling agent. Preferable examples of the charge controlling agent used in combination with the monoazo iron complex compound of the present invention include an azo type iron complex other than the compound of the present invention or its complex salt, an azo type chromium complex or its complex salt, an azo type manganese complex or its complex salt, an azo type cobalt complex or its complex salt, an azo type zirconium complex or its complex salt, a chromium complex of carboxylic acid derivative or its complex salt, a zinc complex of carboxylic acid derivative or its complex salt, an aluminum complex of a carboxylic acid derivative or its complex salt, a zirconium complex of carboxylic acid derivative or its complex salt, and the like. The above carboxylic acid derivative is preferably an aromatic hydroxycarboxylic acid, more preferably 3,5-di-tert-butylsalicylic acid. Further examples include a boron complex or its complex salt, a negatively chargeable resin type charge controlling agent, and the like.

An amount of other charge controlling agent used in combination with the charge controlling agent of the present invention is preferably from 0.1 to 10 mass parts to 100 mass parts of a binder resin.

Examples of a binder resin used in the present invention include known materials usable as a binder resin, e.g. a vinyl polymer of a styrenic monomer, an acrylic monomer, a methacrylic monomer or the like, a copolymer of at least two kinds of these monomers, a polyester type polymer, a polyol resin, a phenol resin, a silicone resin, a polyurethane resin, a polyamide resin, a furan resin, an epoxy resin, a xylene resin, a terpene resin, a coumarone-indene resin, a polycarbonate resin, a petroleum type resin, and the like.

Examples of a styrenic monomer, an acrylic monomer and a methacrylic monomer used for preparing the above vinyl polymer or copolymer are illustrated below, but should not be limited thereto.

Examples of the styrenic monomer include styrenic compounds such as styrene, o-methylstyrene, m-methylstyrene, p-methylstyrene, p-phenylstyrene, p-ethylstyrene, 2,4-dimethylstyrene, p-n-amylstyrene, p-tert-butylstyrene, p-n- hexylstyrene, p-n-octylstyrene, p-n-nonylstyrene, p-n-decylstyrene, p-n-dodecylstyrene, p-methoxystyrene, p-chlorostyrene, 3,4-dichlorostyrene, m-nitrostyrene, o-nitrostyrene, p-nitrostyrene or the like, or their derivatives.

Examples of the acrylic monomer include acrylic acid, or its esters such as methyl acrylate, ethyl acrylate, propyl acrylate, n-butyl acrylate, isobutyl acrylate, n-octyl acrylate, n-dodecyl acrylate, 2-ethylhexyl acrylate, stearyl acrylate, 2-chloroethyl acrylate, phenyl acrylate or the like.

Examples of the methacrylic monomer include methacrylic acid, or its esters such as methacrylic acid, methyl methacrylate, ethyl methacrylate, propyl methacrylate, n-butyl methacrylate, isobutyl methacrylate, n-octyl methacrylate, n-dodecyl methacrylate, 2-ethylhexyl methacrylate, stearyl methacrylate, phenyl methacrylate, diethylaminoethyl methacrylate, diethylaminoethyl methacrylate or the like.

Examples of other monomers usable for preparing the above vinyl monomer or copolymer include the following compounds (1) to (18). (1) Monoolefins such as ethylene, propylene, butylene, isobutylene or the like; (2) polyenes such as butadiene, isoprene or the like; (3) vinyl halides such as vinyl chloride, vinylidene chloride, vinyl bromide, vinyl fluoride, or the like; (4) vinyl esters such as vinyl acetate, vinyl propionate, vinyl benzoate or the like; (5) vinyl ethers such as vinyl methyl ether, vinyl ethyl ether, vinyl isobutyl ether or the like; (6) vinyl ketones such as vinyl methyl ketone, vinyl hexyl ketone, methyl isopropenyl ketone or the like; (7) N-vinyl compounds such as N-vinyl pyrrole, N-vinyl carbazole, N-vinyl indole, N-vinyl pyrrolidone or the like; (8) vinyl naphthalines; (9) acrylic acid or methacrylic acid derivatives such as acrylonitrile, methacrylonitrile, acrylamide or the like; (10) unsaturated dibasic acids such as maleic acid, citraconic acid, itaconic acid, alkenyl succinic acid, fumaric acid, mesaconic acid or the like; (11) unsaturated dibasic acid anhydrides such as maleic anhydride, citraconic anhydride, itaconic anhydride, alkenylsuccinic anhydride or the like; (12) unsaturated dibasic acid monoesters such as maleic acid monomethyl ester, maleic acid monoethyl ester, maleic acid monobutyl ester, citraconic acid monomethyl ester, citraconic acid monoethyl ester, citraconic acid monobutyl ester, itaconic acid monomethyl ester, alkenylsuccinic acid monomethyl ester, fumaric acid monomethyl ester, mesaconic acid monomethyl ester or the like; (13) unsaturated dibasic acid esters such as dimethylmaleic acid, dimethylfumaric acid or the like; (14) α, β-unsaturated acids such as crotonic acid, cinnamic acid or the like; (15) α, β-unsaturated anhydrides such as crotonic anhydride, cinnamic anhydride or the like; (16) monomers having a carboxylic group such as an anhydride of a lower aliphatic acid and the above α, β-unsaturated acid, alkenylmalonic acid, alkenylglutaric acid, alkenyladipic acid, their anhydrides and their monoesters; (17) acrylic acid or methacrylic acid hydroxyalkylesters such as 2-hydroxyethyl acrylate, 2-hydroxyethyl methacrylate, 2-hydroxypropyl methacrylate or the like; and (18) monomers having a hydroxyl group such as 4-(1-hydroxy-1-methylbutyl)styrene, 4-(1-hydroxy-1-methylhexyl)styrene or the like.

In the toner of the present invention, a vinyl polymer or copolymer as a binder resin may have a structure crosslinked by a crosslinking agent having at least 2 vinyl groups, and examples of the crosslinking agent include an aromatic divinyl compound such as divinyl benzene, divinyl naphthalene or the like. Examples of diacrylate compounds bonded by an alkyl chain include ethylene glycol diacrylate, 1,3-butylene glycol diacrylate, 1,4-butane diol diacrylate, 1,5-pentane diol diacrylate, 1,6-hexane diol diacrylate, neopentyl glycol diacrylate, or compounds wherein the acrylates of the above compounds are replaced by methacrylates.

Examples of diacrylate compounds bonded by an alkyl chain containing an ether bond include diethylene glycol diacrylate, triethylene glycol diacrylate, tetraethylene glycol diacrylate, polyethylene glycol #400 diacrylate, polyethylene glycol #600 diacrylate, dipropylene glycol diacrylate, or compounds wherein the acrylates of the above compounds are replaced by methacrylates.

Other examples include diacrylate compounds bonded by a chain containing an ether bond and an aromatic group or their dimethacrylate compounds. Examples of polyester type diacrylates include trade name MANDA (Nippon Kayaku Co., Ltd.).

Examples of a polyfunctional crosslinking agent include pentaerithritol triacrylate, trimethylolethane triacrylate, trimethylolpropane triacrylate, tetramethylolmethane tetraacrylate, oligoester acrylate and compounds wherein the acrylates of the above compounds are replaced by methacrylates, triallyl cyanurate, triallyl trimellitate, and the like.

These crosslinking agents are used preferably in an amount of from 0.01 to 10 mass parts, more preferably from 0.03 to 5 mass parts, to 100 mass parts of other monomer components. Among these crosslinkable monomers, examples preferably usable from viewpoints of a fixing property or an offset resistance include aromatic divinyl compounds (particularly divinyl benzene), diacrylate compounds bonded by a bonding chain containing one ether bond and an aromatic group, and the like. Among these examples, such a combination of monomers as to provide a styrene type copolymer, a styrene-acryl type copolymer or the like are preferable.

Examples of a polymerization initiator used for preparing the vinyl polymer or copolymer of the present invention include 2,2'-azobisisobutyronitrile, 2,2'-azobis(4-methoxy-2,4-dimethylvaleronitrile), 2,2'-azobis(2,4-dimethylvaleronitrile), 2,2'-azobis(2-methylbutyronitrile), dimethyl-2,2'-azobisisobutyrate, 1,1'-azobis(1-cyclohexanecarbonitrile), 2-(carbamoylazo)-isobutyronitrile, 2,2'-azobis(2,4,4-trimethylpentane), 2-phenylazo-2',4'-dimethyl-4'-methoxyvaleronitrile, 2,2'-azobis(2-methylpropane), ketone peroxides such as methyl ethyl ketone peroxide, acetylacetone peroxide, cyclohexanone peroxide or the like, 2,2-bis(tert-butylperoxy)butane, tert-butylhydroperoxide, cumenehydroperoxide, 1,1,3,3-tetramethylbutylhydroperoxide, di-tert-butyl peroxide, tert-butylcumyl peroxide, dicumyl peroxide, α-(tert-butylperoxy)isopropylbenzene, isobutyl peroxide, octanoyl peroxide, decanoyl peroxide, lauroyl peroxide, 3,5,5-trimethylhexanoyl peroxide, benzoyl peroxide, m-tolyl peroxide, di-isopropylperoxy dicarbonate, di-2-ethylhexylperoxy dicarbonate, di-n-propylperoxy dicarbonate, di-2-ethoxyethylperoxy carbonate, diethoxyisopropylperoxy dicarbonate, di(3-methyl-3-methoxybutyl)peroxy carbonate, acetylcyclohexylsulfonyl peroxide, tert-butylperoxy acetate, tert-butylperoxy isobutyrate, tert-butylperoxy-2-ethyl hexalate, tert-butylperoxy laurate, tert-butyl-oxy benzoate, tert-butylperoxyisopropyl carbonate, di-tert-butylperoxy isophthalate, tert-butylperoxyallyl carbonate, isoamylperoxy-2-ethyl hexanoate, di-tert-butylperoxy hexahydroterephthalate, tert-butylperoxy azelate, and the like.

When the binder resin is a styrene-acryl type resin, a resin having a molecular weight distribution of a soluble content of a resin component in tetrahydrofuran (THF) measured by GPC having at least one peak in a zone of a molecular weight of from 3,000 to 50,000 (in terms of number average molecular weight) and at least one peak in a zone of a molecular weight of at least 100,000 is preferable in respect of a fixing property, an offset resistance and a preservability. Also, a preferable binder resin has a molecular weight distribution of the THF-soluble content, in which a component having a molecular weight of at most 100,000 is from 50 to 90%. A more preferable binder resin has a molecular weight distribution having the main peak in a zone of a molecular weight of from 5,000 to 30,000, more preferably from 5,000 to 20,000.

A vinyl polymer such as a styrene-acryl type resin as a binder resin has an acid value of preferably from 0.1 mgKOH/g to 100 mgKOH/g, more preferably from 0.1 mgKOH/g to 70 mgKOH/g, most preferably from 0.1 mgKOH/g to 50 mgKOH/g.

Examples of a monomer used for preparing a polyester type polymer are illustrated below.

Examples of a polyhydric alcohol component include ethylene glycol, propylene glycol, 1,3-butanediol, 1,4-butanediol, 2,3-butanediol, diethylene glycol, triethylene glycol, 1,5-pentanediol, 1,6-hexanediol, neopentyl glycol, 2-ethyl-1,3-hexanediol, hydrogenated bisphenol A, or diols obtained by polymerizing bisphenol A with a cyclic ether such as ethylene oxide or propylene oxide.

It is preferable to use a trihydric or more alcohol in order to crosslink a polyester resin. Examples of the trihydric or more polyhydric alcohol include sorbitol, 1,2,3,6-hexanetetrol, 1,4-sorbitan, pentaerythritol, dipentaerythritol, tripentaerithritol, 1,2,4-butanetriol, 1,2,5-pentatriol, glycerol, 2-methylpropanetriol, 2-methyl-1,2,4-butanetriol, trimethylolethane, trimethylolpropane, 1,3,5-trihydroxybenzene, and the like.

Examples of an acid component for producing the above polyester type polymer include benzene dicarboxylic acids such as phtharic acid, isophthalic acid and terephthalic acid or their anhydrides, alkyl dicarboxylic acids such as succinic acid, adipic acid, sebacic acid and azelaic acid or their anhydrides, unsaturated dibasic acids such as maleic acid, citraconic acid, itaconic acid, alkenylsuccinic acid, fumaric acid and mesaconic acid, unsaturated dibasic acid anhydrides such as maleic anhydride, citraconic anhydride, itaconic anhydride and alkenylsuccinic anhydride, and the like. Also, examples of trivalent or more polyfunctional carboxylic acid components include trimellitic acid, pyromellitic acid, 1,2,4-benzenetricarboxylic acid, 1,2,5-benzenetricarboxyilc acid, 2,5,7-naphthalenetricarboxylic acid, 1,2,4-naphthalenetricarboxylic acid, 1,2,4-butanetricarboxylic acid, 1,2,5-hexanetricarboxylic acid, 1,3-dicarboxy-2-methyl-2-methylenecarboxypropane, tetra(methylenecarboxy)methane, 1,2,7,8-octanetetracarboxylic acid, empole trimer acid or their anhydrides, partly lower alkyl esters, and the like.

When the binder resin is a polyester type resin, a resin having a molecular weight distribution of the THF-soluble content of a resin component having at least one peak in a zone of a molecular weight of from 3,000 to 50,000, is preferable in respect of a fixing property and an offset resistance of a toner, and a more preferable, binder resin has a molecular weight distribution, in which the THF-soluble content includes a component having a molecular weight of at most 100,000 in an amount of from 60 to 100%. A still more preferable binder resin has a molecular weight distribution having at least one peak in a zone of a molecular weight of from 5,000 to 20,000.

When the binder resin is a polyester resin, its acid value is preferably from 0.1 mgKOH/g to 100 mgKOH/g, more preferably from 0.1 mgKOH/g to 70 mgKOH/g, most preferably from 0.1 mgKOH/g to 50 mgKOH/g.

In the present invention, the molecular weight distribution of a binder resin is measured by gel permeation chromatography (GPC) using THF as a solvent.

As a binder resin usable for the toner of the present invention, the above vinyl polymer component and/or polyester type resin component may contain a monomer component reactive with these both resin components. Among monomers constituting the polyester type resin component, examples of a monomer reactive with the vinyl polymer include unsaturated dicarboxylic acids such as phtharic acid, maleic acid, citraconic acid, itaconic acid or their anhydrides. Examples of a monomer constituting the vinyl polymer component include monomers having a carboxyl group or a hydroxyl group, and acrylic acid or methacrylic acid esters.

Also, when using a polyester type polymer, a vinyl polymer and other binder resin in combination, a resin having an acid value of from 0.1 to 50 mgKOH/g of the total binder resin is contained preferably in an amount of at least 60 mass %.

In the present invention, the acid value of a binder resin component of a toner composition is measured by the following method, and its basic operation is carried out in accordance with JIS K-0070.

(1) A sample employed previously excludes additives other than a binder resin (polymer component), or a component other than a binder resin and a crosslinked binder resin is previously measured in respect of an acid value and a content. 0.5 to 2.0 g of a pulverized product of the sample is accurately weighed, and a weight of a polymer component is defined as Wg. For example, when measuring an acid value of a binder resin from a toner, an acid value and a content of a coloring agent, a magnetic material or the like are previously measured, and an acid value of a binder resin is determined by calculation.

(2) The sample is placed in a 300 ml beaker and is dissolved by adding 150 ml of a mixed solution of toluene/ethanol (volume ratio 4/1) thereto.

(3) By using 0.1 mol/l of an ethanol solution of KOH, titration is carried out by using a potential difference titrating apparatus.

(4) An amount of the KOH solution used at this time is defined as S (ml), and a blank sample is measured at the same time, and an amount of the KOH solution used at this time is defined as B (ml), and an acid value is calculated in accordance with the following formula (1). The mark "f" is a factor of KOH.

$$\text{Acid value (mgKOH/g)} = [(S-B) \times f \times 5.61]/W \qquad (1)$$

A binder resin for a toner and a composition containing a binder resin has a glass transition temperature (Tg) of preferably from 35 to 80° C., more preferably from 40 to 75° C., in view of a toner storage property. When the Tg is lower than 35° C., a toner is easily degraded under a high temperature atmosphere, and an offset phenomenon is easily caused at the time of fixing. On the other hand, the Tg exceeds 80° C., there is a tendency that a fixing performance is lowered.

Examples of a magnetic material used in the present invention include (1) a magnetic iron oxide such as magnetite, maghemite or ferrite, and an iron oxide containing other metal oxide, (2) a metal such as iron, cobalt or nickel, or an alloy of these metals with a metal such as aluminum, cobalt, copper, lead, magnesium, tin, zinc, antimony, beryllium, bismuth, cadmium, calcium, manganese, selenium, titanium, tungsten or vanadium, and (3) their mixtures.

Concrete examples of the magnetic material include $Fe_3O_4$, $\gamma$-$Fe_2O_3$, $ZnFe_2O_4$, $Y_3Fe_5O_{12}$, $CdFe_2O_4$, $Gd_3Fe_5O_{12}$, $CuFe_2O_4$, $PbFe_{12}O$, $NiFe_2O_4$, $NdFe_2O$, $BaFe_{12}O_{19}$, $MgFe_2O_4$, $MnFe_2O_4$, $LaFeO_3$, iron powder, cobalt powder, nickel powder and the like. The above-mentioned magnetic materials are used respectively alone or in a mixture of two or more. A particularly preferable magnetic material is a fine powder of triiron tetroxide or $\gamma$-diiron trioxide.

Also, it is possible to use a magnetic iron oxide such as magnetite, maghemite or ferrite or its mixture, which contains other heteroelements. Examples of the other heteroelements include lithium, beryllium, boron, magnesium, aluminum, silicon, phosphorus, germanium, zirconium, tin, sulfur, calcium, scandium, titanium, vanadium, chromium, manganese, cobalt, nickel, copper, zinc, gallium or the like. A preferable heteroelement is selected from the group consisting of magnesium, aluminum, silicon, phosphorus and zirconium. A heteroelement may be incorporated into a crystal lattice of an iron oxide, or may be incorporated as an oxide into an iron oxide, or may be present as an oxide or a hydroxide on the surface, but it is preferable to be contained as an oxide.

The above heteroelements may be incorporated into magnetic particles by making a salt of respective heteroelements present at the time of forming a magnetic material and adjusting a pH value. Also, a heteroelement may be precipitated on the surface of magnetic particles by adjusting a pH value after forming magnetic particles or by adding a salt of respective elements and adjusting a pH value.

The above magnetic material is used in an amount of from 10 to 200 mass parts, preferably from 20 to 150 mass parts, to 100 mass parts of a binder resin. These magnetic materials have a number average particle size of preferably from 0.1 to 2 μm, more preferably from 0.1 to 0.5 μm. The number average particle size can be determined by measuring an enlarged photograph taken by a transmission electron microscope by means of a digitizer or the like.

Also, the magnetic material preferably has magnetic properties of an antimagnetic power of from 20 to 150 oersted, a saturation magnetization of from 50 to 200 emu/g and a residual magnetization of from 2 to 20 emu/g at an application of 10K oersted.

The above magnetic material can be used also as a colorant. In case of a black toner, examples of a colorant usable in the present invention include black or blue dye or pigment particles. Examples of the black or blue pigment include carbon black, aniline black, acetylene black, phthalocyanine blue, indanthrene blue and the like. Examples of the black or blue dye include an azo type dye, an anthraquinone type dye, a xanthene type dye, a methine type dye and the like.

In case of a color toner, examples of a colorant used in the present invention are illustrated below. Examples of a magenta colorant include a condensed azo compound, a diketopyrrolopyrrole compound, an anthraquinone compound, a quinacridon compound, a basic dye, a lake dye, a naphthol dye, a benzimidazolone compound, a thioindigo compound, a perylene compound and the like. More concrete examples of a pigment type magenta colorant include C. I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207 and 209, C. I. Pigment Violet 19, C. I. Vat Red 1, 2, 10, 13, 15, 23, 29 and 35, and the like.

The above pigments may be used respectively alone, but in order to improve clearness, it is preferable to employ a dye and a pigment in combination to provide a satisfactory quality of a full color image.

Examples of a dye type magenta colorant include oil soluble dyes such as C. I. Solvent Red 1, 3, 8, 23, 24, 25, 27, 30, 49, 81, 82, 83, 84, 100, 109, 121, C. I. Disperse Red 9, C. I. Solvent Violet 8, 13, 14, 21, 27, C. I. Disperse Violet 1, and basic dyes such as C. I. Basic Red 1, 2, 9, 12, 13, 14, 15, 17, 18, 22, 23, 24, 27, 29, 32, 34, 35, 36, 37, 38, 39, 40, C. I. Basic Violet 1, 3, 7, 10, 14, 15, 21, 25, 26, 27, 28, and the like.

Examples of a cyane colorant include a copper phthalocyanine compound and its derivative, anthraquinone derivative, anthraquinone, a basic dye lake compound, and the like. Examples of a pigment type cyane colorant include C. I. Pigment Blue, 2, 3, 15, 16 and 17, C. I. Vat Blue 6, C. I. Acid Blue 45 or a copper phthalocyanine pigment substituting 1 to 5 phthalimidomethyl groups into a phthalocyanine structure.

Examples of a yellow colorant include a condensed azo compound, an isoindolinone compound, an anthraquinone compound, an azo metal complex, a methine compound, an allyl amido compound, and the like. Concrete examples of a yellow pigment include C. I. Pigment Yellow 1, 2, 3, 4, 5, 6, 7, 10, 11, 12, 13, 14, 15, 16, 17, 23, 65, 73 and 83, C. I. Vat Yellow 1, 3 and 20, and the like.

The above colorant is used preferably in an amount of from 0.1 to 20 mass parts to 100 mass parts of a binder resin.

The toner of the present invention may be used as a two-component developer by mixing with a carrier. Examples of the carrier used in the present invention include a usual carrier such as ferrite, magnetite or the like, and a resin-coated carrier.

The resin-coated carrier comprises carrier core particles and a resin coating material coated on the surface of the carrier core particles, and examples of the resin used as the coating material include a styrene-acryl type resin such as a styrene-acrylic acid ester copolymer, styrene-methacrylic acid ester copolymer or the like, an acrylic resin such as acrylic acid ester copolymer, methacrylic acid ester copolymer or the like, a fluorine-containing resin such as polytetrafluoroethylene, monochlorotrifluoroethylene polymer, polyvinylidene fluoride or the like, a silicone resin, a polyester resin, a polyamide resin, a polyvinyl butyral, an aminoacrylate resin, or the like, and other examples include an iomonomer resin, a polyphenylene sulfide resin or the like, which may be usable as a coating material for a carrier, and these resins may be used respectively alone or in a mixture of two or more.

Also, a binder type carrier core having a magnetic powder dispersed in a resin may be used.

In a resin-coated carrier, examples of a method for coating a resin on the surface of a carrier core include a method for coating a carrier core by coating with a solution or dispersion having a resin dissolved or dispersed, or a method of simply mixing a resin and a carrier in a powdery state. A ratio of a resin coating material to a resin-coated carrier may be optionally determined, but an amount of a resin is preferably from 0.01 to 5 mass %, more preferably from 0.1 to 1 mass %, to a resin-coated carrier.

Examples of a case of coating a magnetic material with a mixture of two or more coating materials include (1) to treat 100 mass parts of a titanium fine powder with 12 mass parts of a mixture of dimethyl dichlorosilane and dimethyl silicone oil (mass ratio 1:5), and (2) to treat 100 mass parts of a silica fine powder with 20 mass parts of a mixture of dimethyl dichlorosilane and dimethyl silicone oil (mass ratio 1:5).

Among the above resins, a styrene-methyl methacrylate copolymer, a mixture of a fluorine-containing resin and a styrenic copolymer, or a silicone resin is preferably used, and a silicone resin is particularly preferable.

Examples of a mixture of a fluorine-containing resin and a styrenic copolymer include a mixture of polyvinylidene fluoride and styrene-methyl methacrylate copolymer, a mixture of polytetrafluoroethylene and styrene-methyl methacrylate copolymer, and a mixture of vinylidene fluoride-tetrafluoroethylene copolymer (copolymer mass ratio 10:90–90:10), styrene-2-ethylhexyl acrylate copolymer (copolymer mass ratio 10:90–90:10) and styrene-2-ethylhexyl acrylate-methyl methacrylate copolymer (copolymer mass ratio 20–60:5–30:10–50).

Examples of the silicone resin include a nitrogen-containing silicone resin, a modified silicone resin formed by reacting a silicone resin with a nitrogen-containing silane coupling agent, and the like.

Examples of a magnetic material for a carrier core include an oxide such as ferrite, iron-excessive type ferrite, magnetite, γ-iron oxide or the like, a metal such as iron, cobalt, nickel or the like, or their alloys. Also, examples of an element contained in these magnetic materials include iron, cobalt, nickel, aluminum, copper, lead, magnesium, tin, zinc, antimony, beryllium, bismuth, calcium, manganese, selenium, titanium, tungsten, vanadium and the like. Preferable examples include a copper-zinc-iron type ferrite containing copper, zinc and iron as main components, and a manganese-magnesium-iron type ferrite containing manganese, magnesium and iron as main components.

A resistance value of a carrier is adjusted to be preferably from $10^6$ to $10^{10}$ Ω·cm by adjusting an amount of a coated resin and a concave convex degree of the surface of a carrier. A carrier having a particle size of from 4 to 200 μm is usable, but a carrier has a particle size of preferably from 10 to 150 μm, more preferably from 20 to 100 μm. Particularly, 50% of a resin-coated carrier should have preferably a particle size of from 20 to 70 μm.

A two-component system developer contains the toner of the present invention in an amount of preferably from 1 to 200 mass parts, more preferably from 2 to 50 mass parts, to 100 mass parts of a carrier.

The toner of the present invention may further contain a wax. The wax usable in the present invention is illustrated below, examples of which include an aliphatic hydrocarbon type wax such as low molecular weight polyethylene, low molecular weight polypropylene, polyolefin wax, microcrystalline wax, paraffin wax, southall wax or the like, an oxide of an aliphatic hydrocarbon type wax such as polyethylene wax oxide or the like, or their block copolymers, a plant type wax such as candelilla wax, carnauba wax, haze wax, jojoba wax or the like, an animal type wax such as bee wax, lanoline, whale wax or the like, a mineral type wax such as ozokerite, ceresin, petrolactum or the like, a wax containing an aliphatic acid ester as the main component such as montanic acid ester wax, castor wax or the like, a wax, a part or all part of which are deacidified such as deacidified carnauba wax, or the like.

Concrete examples of the wax include saturated linear chain aliphatic acids such as palmitic acid, stearic acid, montanic acid or linear chain alkyl carboxylic acids having a linear chain alkyl group; unsaturated aliphatic acids such as planzic acid, eleostearic acid or parinaric acid; saturated alcohols such as stearyl alcohol, eicosyl alcohol, behenyl alcohol, carnaubyl alcohol, ceryl alcohol, mesyl alcohol or a long chain alkyl alcohol; polyhydric alcohols such as sorbitol; aliphatic acid amides such as linolic acid amide, olefinic acid amide or lauric acid amide; saturated aliphatic acid bis-amides such as methylene bis-capric acid amide, ethylene bis-lauric acid amide or hexamethylene bis-stearic acid amide; unsaturated aliphatic acid amides such as ethylene bis-oleic acid amide, hexamethylene bis-oleic acid amide, N,N'-dioleyl adipic acid amide or N,N'-dioleyl sebacic acid amide; aromatic bis-amides such as m-xylene bis-stearic acid amide or N,N-distearyl isophtharic acid amide; aliphatic acid metal salts such as calcium stearate, calcium laurate, zinc stearate or magnesium stearate; a wax having a vinyl type monomer (such as styrene or acrylic acid) grafted with an aliphatic hydrocarbon type wax; a partly esterified compound of a polyhydric alcohol with an aliphatic acid such as behenic acid mono glyceride; a methyl esterified compound having a hydroxyl group obtained by hydrogenating a plant oil; and the like.

Preferable examples of the wax include a polyolefin obtained by having an olefin radical polymerized under a high pressure; a polyolefin obtained by purifying a low molecular weight by-product obtained at the time of polymerizing a high molecular weight polyolefin; a polyolefin obtained by polymerizing by using a catalyst such as a Ziegler catalyst or a metallocene catalyst under a low pressure; a polyolefin obtained by polymerizing by means of radiation, electromagnetic wave or light; a low molecular weight polyolefin obtained by thermally decomposing a high molecular weight polyolefin; a paraffin wax, a microcrystalline wax, a Fischer-Tropsch wax; a synthetic hydrocarbon wax synthesized by zyntol method, hydrocol method, Age method or the like; a synthetic wax obtained from a monomer of a compound having a carbon number of 1; a hydrocarbon wax having a functional group such as a hydroxyl group or a carboxyl group; a mixture of a hydrocarbon wax and a hydrocarbon wax having a functional group; a modified wax obtained by using these waxes as a matrix and graft-modifying with a vinyl monomer such as styrene, maleic acid ester, acrylate, methacrylate or maleic anhydride; and the like.

Before using, these wax may be treated preferably by press-sweating method, solvent method, recrystallization method, vacuum distillation method, supercritical gas extraction method or solution-precipitation method to make their molecular weight distributions sharp or to remove a low molecular weight solid aliphatic acid, a low molecular weight solid alcohol, a low molecular weight solid compound and other impurities.

In order to make a good balance between a fixing property and an offset resistance, the wax used in the present invention preferably has a melting point of from 70 to 140° C., more preferably from 70 to 120° C. If the melting point is lower than 70° C., an antiblocking property tends to be lowered, and if the melting point exceeds 140° C., the offset resistance effect is hardly achieved.

Also, by using at least two kinds of waxes in combination, a plasticizing function and a releasing function can be achieved at the same time.

Examples of a wax having a plasticizing function include a wax having a low melting point, a wax having a branched molecular structure or a wax having a structure having a polar group, and examples of a wax having a releasing function include a wax having a high melting point, a wax having a linear chain structure or a non-polar wax having no functional group. Use examples of a combination of waxes include a combination of waxes having a melting point difference of from 10° C. to 100° C., a combination of a polyolefin and a graft-modified polyolefin, or the like.

When electing two kinds of waxes having similar structures, a wax having a relatively lower melting point achieves a plasticizing function and a wax having a relatively higher melting point achieves a releasing function. In this case, when the melting point difference is in a range of from 10 to 100° C., respective functions are separately and effectively achieved. When the melting point difference is less than 10° C., it becomes hard to achieve respectively separate functions, and if the melting point difference exceeds 100° C., well-balanced mutual functions are hardly achieved. In this case, if at least one of the waxes has a melting point of preferably from 70 to 120° C., more preferably from 70 to 100° C., an effect of achieving respectively separate functions tends to be easily achieved.

A wax having a relatively branched structure, a wax having a polar group such as a functional group or a wax modified by a component different from the main component, achieves a plasticizing function, while a wax having a linear chain structure, a non-polar wax having no functional group or an unmodified straight wax, achieves a releasing function. Examples of a preferable combination include a combination of a polyethylene homopolymer comprising ethylene as the main component or its copolymer and a polyolefin homopolymer comprising olefin other than ethylene as the main component or its copolymer; a combination of a polyolefin and a graft-modified polyolefin; a combination of an alcohol wax, an aliphatic acid wax or an ester wax and a hydrocarbon type wax; a combination of a Fischer-Tropsh wax or a polyolefin wax and a paraffin wax or a microcrystalline wax; a combination of a Fischer-Tropsh wax was and a polyolefin wax; a combination of a paraffin wax and a microcrystalline wax; a combination of a carnauba wax, a candelilla wax, a rice wax or montan wax and a hydrocarbon type wax; and the like.

In each case, it is preferable that a heat-absorbing peak observed by DSC measurement of a toner becomes a maximum peak of peak top temperature in a zone of from 70 to 120° C., preferably in a zone of from 70 to 110° C. In this manner, the toner has well balanced storage stability and fixing property.

In the toner of the present invention, a total content of these waxes is effectively from 0.2 to 20 mass parts, preferably from 0.5 to 10 mass parts, to 100 mass parts of a binder resin.

In the present invention, a peak top temperature of the maximum peak of a heat-absorbing peak of wax measured by DSC is defined as a melting point of wax.

In the present invention, the DSC measurement of wax or toner is carried out preferably by using a high accuracy internal heating system input compensation type differential scanning calorimeter. The measuring method is carried out in accordance with ASTM D3418-82. The DSC curve used in the present invention is a DSC curve measured at the time of raising a temperature at a rate of 10° C./min after taking a previous history of one time temperature rising-temperature lowering.

Further, the toner of the present invention may contain a fluidity-improving agent. By adding the fluidity-improving agent to the surface of the toner, a fluidity is improved (the toner becomes easily flowable). Examples of the fluidity-improving agent include carbon black, a fluorine type resin powder such as vinylidene fluoride fine powder, polytetrafluoroethylene fine powder or the like, a silica fine powder such as wet process-produced silica or dry process-produced silica, a titanium oxide fine powder, an alumina fine powder, and a treated silica, a treated titanium oxide or a treated alumina, which is surface-treated with a silane coupling agent, a titanium coupling agent or a silicone oil. Among them, preferable examples include a silica fine powder, a titanium oxide fine powder and an alumina fine powder, or a treated silica, the surface of which is treated with a silane coupling agent or a silicone oil. The fluidity-improving agent preferably has an average primary particle size in a range of from 0.001 to 2 μm, more preferably in a range of from 0.002 to 0.2 μm.

A preferable silica fine powder is a fine powder obtained by vapor phase oxidation of a silicon halide compound such as dry process-produced silica or fumed silica.

A silica fine powder produced by vapor phase oxidation of a silicon halide compound is commercially available under the following trade names: AEROSIL 130 (manufactured by Nihon Aerosil K.K.), AEROSIL 300 (manufactured by Nihon Aerosil K.K.), AEROSIL 380 (manufactured by Nihon Aerosil K.K.), AEROSIL TT600 (manufactured by Nihon Aerosil K.K.), AEROSIL MOX170 (manufactured by Nihon Aerosil K.K.), AEROSIL MOX80 (manufactured by Nihon Aerosil K.K.), AEROSIL COK84 (manufactured by Nihon Aerosil K.K.), Ca—O—SiL M-5 (manufactured by CABOT Co.), Ca-O-SiL MS-7 (manufactured by CABOT Co.), Ca—O—SiL MS-75 (manufactured by CABOT Co.), Ca—O—SiL HS-5 (manufactured by CABOT Co.), Ca—O—SiL EH-5 (manufactured by CABOT Co.), Wacker HDK N20 (manufactured by WACKER-CHEMIEGMBH), Wacker HDK V15 (manufactured by WACKER-CHEMIEGMBH), Wacker HDK N20E (manufactured by WACKER-CHEMIEGMBH), Wacker HDK T30 (manufactured by WACKER-CHEMIEGMBH), Wacker HDK T40 (manufactured by WACKER-CHEMIEGMBH), D-C Fine-Silica (Dow Corning Co.), Fransol (Fransil Co.), and the like.

Further, a treated silica fine powder of the above silicone halide compound obtained by gas phase oxidation of the silicone halide compound and subjected to hydrophobic treatment is more preferable. Still further, among the treated silica fine powders, a silica fine powder treated so as to have a hydrophobicity (hydrophobic degree) of in a range of from 30 to 80 measured by methanol titration test is particularly preferable. The hydrophobic treatment is carried out by chemically or physically treating a silica fine powder with an organic silicon compound reactive or physically adsorptive with the silica fine powder. As a preferable treatment process, a silica fine powder obtained by subjecting a silica halide compound to gas phase oxidation is treated with an organic silicon compound.

Examples of the organic silicon compound include hydroxypropyltrimethoxysilane, phenyltrimethoxysilane, n-hexadecyltrimethoxysilane, n-octadecyltrimethoxysilane, vinylmethoxysilane, vinylethoxysilane, vinyltriacetoxysilane, dimethylvinylchlorosilane, divinylchlorosilane, γ-methacryloxypropyltrimethoxysilane, hexamethyldisilane, trimethylsilane, trimethylchlorosilane, dimethyldichlorosilane, methyltrichlorosilane, allyldimethylchlorosilane, allylphenyldichlorosilane, benzyldimethylchlorosilane, bromomethyldimethylchlorosilane, α-chloroethyltrichlorosilane, β-chloroethyltrichlorosilane, chloromethyldimethylchlorosilane, triorganosilylmercaptan, trimethylsilylmercaptan, triorganosilylacrylate, vinyldimethylacetoxysilane, dimethylethoxysilane, trimethylethoxysilane, trimethylmethoxysilane, methyltriethoxysilane, isobutyltrimethoxysilane, dimethyldimethoxysilane, diphenyldiethoxysilane, hexamethyldisiloxane, 1,3-divinyltetramethyldisiloxane, 1,3-diphenyltetramethyldisiloxane and dimethylpolysiloxane having 2 to 12 siloxane units per molecule and also having 0 to 1 hydroxyl group bonded respectively to one Si in the terminal. A further example includes a silicone oil such as dimethylsilicone oil. They are used respectively alone or in a mixture of two or more.

A fluid-improving agent has a number average particle size of preferably 5 to 100 nm, more preferably 5 to 50 nm. A fluidity-improving agent having a specific surface area of at least 30 $m^2/g$, preferably 60 to 400 $m^2/g$, measured on the basis of nitrogen adsorption measured by BET method, and having a specific surface area of preferably at least 20 $m^2/g$, more preferably 40 to 300 $m^2/g$ as a treated fine powder, provides a satisfactory result. The fluidity-improving agent is used preferably in an amount of from 0.03 to 8 parts by mass per 100 parts by mass of a toner.

The toner of the present invention may further contain other additives such as various metal soaps, a fluorine type surfactant, dioctyl phthalate and the like, in order to protect a photosensitive material and a carrier, to improve a cleaning property, to adjust thermal, electric or physical properties, to adjust a resistance, to adjust a softening point, to improve a fixing rate, or the like, and may further include an electroconductivity-imparting agent such as tin oxide, zinc oxide, carbon black and antimony oxide, and inorganic fine powders such as titanium oxide, aluminum oxide and alumina, and the like. Also, these inorganic fine powders may be optionally subjected to hydrophobic treatment. Also, the toner may further contain a lubricant such as polytetrafluoroethylene, zinc stearate, or vinylidene polyfluoride, an abradant such as cesium oxide, silicon carbide or strontium titanate, an anti-caking agent, and a development-improving agent such as black fine particles and white fine particles having a reverse polarity to the toner particles in a small amount.

In order to control a charging amount, these additives are preferably treated with various treating agents including a silicone varnish, various modified silicone varnishes, a silicone oil, various modified silicone oils, a silane coupling agent, a silane coupling agent having a functional group, and other organic silicon compounds, or other treating agents.

The charge controlling agent of the present invention, the above-mentioned additives and a toner are fully mixed and stirred by a mixer such as a Henschel mixer, a ball mill, a Nowter mixer, a V type mixer, a W type mixer, a super mixer, or the like to have the surface of toner particles uniformly treated with the above additives, thereby obtaining a desired electrostatic image developing toner.

The toner of the present invention is thermally stable and can retain a stable chargeability without being susceptive to a thermal change. Also, since it is uniformly dispersed in any binder resin, a charge distribution of a fresh toner becomes very uniform, and the toner of the present invention including untransferred and recovered toner (used toner) does not provide a substantial change in a saturated tribo-charged amount and a charge distribution as compared with a fresh toner. When a used toner provided from the electrostatic image developing toner of the present invention is reused, it is possible to further make a difference between the fresh toner and the used toner smaller by preparing a toner using a polyester resin including an aliphatic diol as a binder resin or a metal-crosslinked styrene-acryl copolymer as a binder resin and also using a large amount of polyolefin added thereto.

The toner of the present invention can be prepared by a known preparation method. For instance, the above-mentioned starting materials for preparing a toner, such as a binder resin, a charge controlling agent, a coloring agent and the like, are fully mixed by a mixer such as a ball mill. As a preferable method, the mixture thus obtained is fully kneaded by a heating kneader such as a heat roll kneader, cooled to be solidified, pulverized and classified (pulverizing method).

Also, the above obtained mixture may be dissolved in a solvent, sprayed to make fine particles, dried and classified. Further examples include a method for preparing a toner by polymerization method which comprises mixing predetermined starting materials with a monomer for constituting a binder resin to prepare an emulsion or suspension liquid and then polymerizing the liquid, and a method for preparing a microcapsule toner made of a core material and a shell material, which comprises incorporating predetermined starting materials into the core material or the shell material or both of the two materials. Further, if necessary, desired additives and toner particles may be fully mixed by a mixer such as a Henschel mixer to prepare the toner of the present invention.

A method for preparing the toner of the present invention by the above-mentioned pulverizing method is described in more details. First, a binder resin, a coloring agent, a charge controlling agent and other necessary additives are uniformly mixed. The mixing can be carried out by a known stirrer such as a Henschel mixer, a super mixer, a ball mill or the like. The mixture thus obtained is hot melt-kneaded by a sealed type kneader or a monoaxial or biaxial extruder. The kneaded product is cooled, roughly pulverized by a crusher or a hammer mill, and is further finely pulverized by a pulverizing machine such as a jet mill, a high speed rotor rotation type mill or the like. The finely pulverized product is then classified by a wind power classifier, an inertia-classifying system elbow jet using a Coanda effect, a cyclone (centrifugal type) classifying system Microplex, a DS separator or the like to classify the particles into a predetermined particle size. Further, when treating a toner surface with an additive, the toner and the additive are stirred and mixed by a high speed stirrer such as a Henschel mixer, a super mixer or the like.

Also, the toner of the present invention can be prepared by suspension polymerization method or emulsion polymerization method. In the suspension polymerization method, a polymerizable monomer, a coloring agent, a polymerization initiator, a charge controlling agent, a crosslinking agent (if necessary) and other additives are uniformly dissolved or dispersed to prepare a monomer composition, and the monomer composition thus prepared is dispersed into a continuous phase containing a dispersion stabilizer such as an aqueous phase by an appropriate stirrer and a dispersing machine such as a homomixer, a homogenizer, an atomizer, a microfluidizer, a mono-liquid fluid nozzle, a gas-liquid fluid nozzle, an electric emulsifier or the like. Preferably, a stirring speed, a temperature and a time are adjusted in such a manner as to provide droplets of the polymerizable monomer composition suitable for producing toner particles having a desired particle size. At the same time, the polymerization reaction is carried out at 40 to 90° C., thereby producing toner particles having a desired particle size. The toner particles thus obtained are washed and filtrated, and are dried. After preparing toner particles as mentioned above, the toner particles may be treated by an additive in accordance with the above-mentioned method.

The toner particles prepared by the emulsion polymerization method are excellent in uniformity, but have a very small average particle size of from 0.1 to 1.0 µm as compared with the toner particles prepared by the suspension polymerization method. Accordingly, if necessary, it is possible to employ a seed polymerization method which comprises using emulsified particles as a seed core and adding a polymerizable monomer thereto to grow particles or a method for combining emulsified particles into a desired average particle size and melt-bonding.

It is not necessary for these preparation methods by polymerization to impart brittleness to toner particles since a pulverizing step is not employed, and it is possible to employ a low softening point material in a large amount which is hardly used for a conventional pulverizing method. Thus, it is possible for these polymerization methods to widely employ various starting materials. Also, such a releasing agent as a hydrophobic material or a coloring agent is hardly exposed on the surface of toner particles, and consequently they do not contaminate a toner-supporting element, a photosensitive material, a transferring roller, a fixing device or the like.

By preparing the toner of the present invention by a polymerization method, various properties such as an image reproducibility, a transferring property or a color reproducibility can be further improved, and it is possible to make a toner particle size smaller so as to be suitable for reproducing very fine dots and a toner having a sharp particle size distribution can be relatively easily produced.

A radical-polymerizable vinyl type polymerizable monomer is used as a polymerizable monomer used in the preparation of the toner of the present invention by a polymerization method. The vinyl type polymerizable monomer includes a monofunctional polymerizable monomer or a polyfunctional polymerizable monomer.

Examples of the monofunctional polymerizable monomer include a styrene type polymerizable monomer such as styrene, α-methylstyrene, β-methylstyrene, o-methylstyrene, m-methylstyrene, p-methylstyrene, 2,4-dimethylstyrene, p-n-butylstyrene, p-tert-butylstyrene, p-n-hexylstyrene, p-phenylstyrene or the like; an acryl type polymerizable monomer such as methyl acrylate, ethyl acrylate, n-propyl acrylate, isopropyl acrylate, n-butyl acrylate, isobutyl acrylate, tert-butyl acrylate, n-amyl acrylate, n-hexyl acrylate, 2-ethylhexyl acrylate, n-octyl acrylate, benzyl acrylate, dimethylphosphate methyl acrylate, dibutylphosphate ethyl acrylate, 2-benzoyloxyethyl acrylate, or the like; a methacryl type polymerizable monomer such as methyl methacrylate, ethyl methacrylate, n-propyl methacrylate, isopropyl methacrylate, n-butyl methacrylate, isobutyl methacrylate, tert-butyl methacrylate, n-amyl methacrylate, n-hexyl methacrylate, 2-ethylhexyl methacrylate, n-octyl methacrylate, diethylphosphate methacrylate, dibutylphosphate ethyl methacrylate, or the like; unsaturated aliphatic monocarboxylic acid esters; vinyl esters such as vinyl acetate, vinyl propionate, vinyl benzoate or the like; vinyl ethers such as vinyl methyl ether, vinyl isobutyl ether or the like; vinyl ketones such as vinyl methyl ketone, vinyl hexyl ketone, vinyl isopropyl ketone or the like; and the like.

Examples of the polyfunctional polymerizable monomer include diethylene glycol diacrylate, triethylene glycol diacrylate, tetraethylene glycol diacrylate, polyethylene glycol diacrylate, 1,6-hexanediol diacrylate, neopentyl glycol diacrylate, tripropylene glycol diacrylate, polypropylene glycol diacrylate, 2,2-bis[4-(acryloxy.diethoxy)phenyl]propane, trimethylpropane triacrylate, tetramethylolmethane tetraacrylate, ethylene glycol dimethacrylate, triethylene glycol dimethacrylate, tetraethylene glycol dimethacrylate, polyethylene glycol dimethacrylate, 1,3-butylene glycol dimethacrylate, 1,6-hexanediol dimethacrylate, neopentyl glycol methacrylate, polypropylene glycol dimethacrylate, 2,2-bis[4-(methacryloxy.diethoxy)phenyl]propane, 2,2-bis [4-(methacryloxy.polyethoxy)phenyl]propane, trimethylolpropane trimethacrylate, tetramethylolmethane tetramethacrylate, divinylbenzene, divinylnaphthalene, divinylether, or the like.

In the present invention, the above-mentioned monofunctional polymerizable monomer may be used alone or in combination of two or more, and the monofunctional polymerizable monomer and the polyfunctional polymerizable monomer may be used in combination. Also, the above-mentioned polyfunctional polymerizable monomer may be used as a crosslinking agent. A polymerizable initiator used for polymerizing the above polymerizable monomers includes an oil-soluble initiator and/or a water-soluble initiator. Examples of the oil-soluble initiator include an azo compound such as 2,2'-azobisisobutyronitrile, 2,2'-azobis-2,4-dimethylvaleronitrile, 1,1'-azobis(cyclohexane-1-carbonitrile), 2,2'-azobis-4-methoxy-2,4-dimethylvaleronitrile or the like; and a peroxide type initiator such as acetylcyclohexylsulfonyl peroxide, diisopropyl peroxycarbonate, decanoyl peroxycarbonate, decanoyl peroxide, propionyl peroxide, acetyl peroxide, tert-butylperoxy-2-ethylhexanoate, benzoyl peroxide, tert-butylperoxy isobutyrate, cyclohexanone peroxide, methyl ethyl ketone peroxide, tert-butyl peroxide, di-tert-butyl peroxide, cumene hydroperoxide or the like; and the like.

Examples of the water-soluble initiator include ammonium persulfate, potassium persulfate, 2,2'-azobis(N,N'-dimethyleneisobutyroamidine)hydrochloride, 2,2'-azobis(2-aminodipropane)hydrochloride, azobis(isobutylamidine) hydrochloride, sodium 2,2'-azobisisobutyronitrile sulfonate, ferrous sulfate or hydrogen peroxide.

The polymerization initiator is used alone or in a combination in an amount of from 0.5 to 20 mass parts to 100 mass parts of a polymerizable monomer.

Examples of a dispersant used in the preparation of a polymerization toner include inorganic oxides such as tricalcium phosphate, magnesium phosphate, aluminum phosphate, zinc phosphate, calcium carbonate, magnesium carbonate, aluminum hydroxide, calcium metasilicate, calcium sulfate, barium sulfate, bentonite, silica, alumina and the like. Examples of an organic compound used as a dispersant include polyvinyl alcohol, gelatin, methyl cellulose, methylhydroxypropyl cellulose, ethyl cellulose, carboxymethyl cellulose sodium salt, starch, and the like. These dispersants are used preferably in an amount of from 0.2 to 2.0 mass parts to 100 mass parts of a polymerizable monomer.

Commercially available materials may be used as they are for these dispersants, but the above-mentioned inorganic compounds may be formed in a dispersion medium under high speed stirring in order to obtain dispersion particles having a fine uniform particle size.

The toner obtained by the above polymerization method tends to provide toner particles having a smaller concavo-convex degree as compared with a toner obtained by pulverizing method without any special treatment, and since they are in an indeterminate form, they increase a contact area between an electrostatic latent image-supporting element and the toner particles and consequently provide various advantages of enhancing a toner-attaching force, consequently not contaminating the inside of a copying machine, providing a higher image density and producing an image of high quality.

Also, a toner prepared by pulverizing method may be treated to reduce a concavo-convex degree of the toner surface by a hot bath method of dispersing toner particles in water and heating, a heat treating method by passing toner particles through a hot air stream, or a mechanically impacting method of treating toner particles by imparting a mechanical energy to them. Examples of an apparatus effective for reducing a concavo-convex degree include a mechanofusion system (manufactured by Hosokawamicron Corporation) employing a dry type mechanochemical method, an I system jet mill, a hybridizer (manufactured by Nara Machinery Co., Ltd.) which is a mixing apparatus having a rotor and a liner, a Henschel mixer which is a mixer having a high speed stirring blade, and the like.

A concavo-convex degree of the toner particles can be expressed by an average circularity which is an index for indicating a concavo-convex degree. The average circularity (C) is a value determined by measuring a circularity (Ci) in accordance with the following formula (2) and dividing the total sum of the measured circularity values of all particles by the number of all particles (m) in accordance with the following formula (3).

$$\text{Circularity } (Ci) = \frac{\text{Circumference length of circle having the same projected area as particle}}{\text{Circumference length of projected area of particle}} \quad (2)$$

$$\text{Average circularity } C = \sum_{i=1}^{m} Ci/m \quad (3)$$

The above circularity (Ci) is measured by using a flow type particle image-analyzing apparatus (such as EPIA-1000 manufactured by Sysmex Corporation). The measuring method comprises preparing a dispersion solution having about 5 mg of a toner dispersed in 10 ml of water having about 0.1 mg of a nonionic surfactant dissolved, irradiating the dispersion solution with ultrasonic wave (20 kHz, 50 W) for 5 minutes to prepare a dispersion having a dispersion concentration of 5,000 to 20,000 pieces/μ liter and measuring a circularity distribution of particles having a sphere-equivalent particle size of from 0.60 μm to 159.21 μm by the above flow type particle image-measuring apparatus.

By adjusting toner particles so as to have the above average circularity value of preferably from 0.955 to 0.990, more preferably from 0.960 to 0.985, it becomes possible to reduce an amount of a remaining toner after transferring and to prevent re-transferring.

In the toner of the present invention, in view of image property and productivity of the toner, the toner should preferably have an average particle size based on volume in the range of from 2 to 15 μm as measured by a laser type particle size distribution-measuring machine such as micronsizer (manufactured by Seishin Kigyo K.K.). A more preferable average particle size is in a range of from 3 to 12 μm. If the average particle size exceeds 15 μm, resolving power and sharpness become poor, and if the average particle size is less than 2 μm, the resolving power is satisfactory, but a yield of toner production becomes low and a production cost becomes high, and various tendency that a problem of scattering of a toner in a machine and a health problem due to invasion of a toner into a human skin are caused.

With regard to a particle size distribution of the toner of the present invention, by measuring a particle size by a COULTER COUNTER (TA-II manufactured by COULTER Co.), a content of particles having a particle size of at most 2 μm is preferably in a range of from 10 to 90% on the basis of the number of particles, and a content of particles having a particle size of at least 12.7 μm is preferably in a range of from 0 to 30% on the basis of volume.

The electrostatic image developing toner of the present invention preferably has a specific surface area in a range of from 1.2 to 5.0 $m^2/g$, more preferably in a range of from 1.5 to 3.0 $m^2/g$, as measured by BET specific surface area measurement using nitrogen as a desorption-adsorption gas. The measurement is carried out by using a BET specific surface area measuring apparatus (Flow SorbII2300, manufactured by Shimadzu Seisakusyo K.K.), and a specific surface area is defined as a value determined from a desorbed gas amount measured by desorbing an adsorbed gas on a toner surface at 50° C. for 30 minutes, adsorbing a nitrogen gas again by rapidly cooling with liquid nitrogen, and heating to 50° C. again for carrying out desorption again.

An apparent specific gravity (bulk density) of the toner of the present invention is measured by using a powder tester (manufactured by Hosokawa Micron K.K.). When the toner of the present invention is a non-magnetic toner, the toner should preferably have an apparent specific gravity of from 0.2 to 0.6 g/cc, and when the toner of the present invention is a magnetic toner, the toner should preferably have an apparent specific gravity of from 0.2 to 2.0 g/cc although it may vary depending on a content and a type of a magnetic powder used.

When the toner of the present invention is a non-magnetic toner, a toner should preferably have a true specific gravity of from 0.9 to 1.2 g/cc, and when the toner is a magnetic toner, the toner should preferably have a true specific gravity of from 0.9 to 4.0 g/cc although it varies depending on a content and a type of a magnetic powder used. The true specific gravity of the toner is measured by accurately measuring a weight of 1.000 g of toner, placing the measured toner in a 10 mmφ tablet-molding machine, press-molding under a pressure of $196 \times 10^5$ Pa (200 kgf/cm$^2$) in vacuum, and measuring a height of the molded product of cylindrical shape by a micrometer, thereby calculating a true specific gravity.

A fluidity of a toner is defined as a flow angle of repose and a static angle of repose measured by a repose angle-measuring apparatus (manufactured by Tsutsui Rika K.K.). The electrostatic image developing toner using a charge control agent of the present invention preferably has a flow angle of repose of from 5° to 45° and a static angle of repose of from 10° to 50°.

In case of a pulverized type toner, the toner of the present invention should preferably have a shape coefficient (SF-1) of from 100 to 400 and a shape coefficient (SF-2) of from 100 to 350.

In the present invention, shape coefficients SF-1 and SF-2 of a toner are calculated by sampling a group of about 30 product particles as an image enlarged 1,000 times in one view by an optical microscope (such as BH-2, manufactured by Olympus Optical Co., Ltd.) equipped with a CCD camera, and transferring obtained images to an image analyzing apparatus (such as Luzex FS® manufactured by Nireko K.K.). The same operation is repeated until measuring about 1,000 particles of one product, and shape coefficients SF-1 and SF-2 of each toner are expressed by average values of measured values of all particles.

$$SF\text{-}1 = \{(ML^2 \times \pi)/4A\} \times 100$$

(In the above formula, ML is a maximum length of a particle and A is a projected area of one particle.)

$$SF\text{-}2 = (PM^2/4A\pi) \times 100$$

(In the above formula, PM is a circumference length of a particle and A is a projected area of one particle.)

SF-1 expresses a strain of a particle, and if a particle becomes closer to a sphere, an SF-1 value becomes closer to 100, and if this value becomes larger, a particle becomes longer and narrower. On the other hand, SF-2 expresses an irregularity degree of a particle surface, and if a particle becomes closer to a sphere, an SF-2 value becomes closer to 100, and if a particle shape becomes more complicated, an SF-2 value becomes larger.

The electrostatic image developing toner of the present invention preferably has a volume resistivity of from $1\times10^{12}$ to $1\times10^{16}$ Ω·cm in a case of a non-magnetic toner and also has a volume resistivity of from $1\times10^8$ to $1\times10^{16}$ Ω·cm in a case of a magnetic toner although it varies depending on a content and a type of a magnetic powder used. The volume resistivity of the toner is measured by pressure-molding toner particles into a disk-like test piece having a diameter of 50 mm and a thickness of 2 mm, fixing the test piece on an electrode for solid (SE-70 manufactured by Ando Denki K.K.), and measuring a resistance value one hour after continuously applying a direct current voltage of 100 V by using a high insulating resistance meter (4339A manufactured by Hughlet Packard Co.).

The toner of the present invention preferably has a dielectric dissipation factor of from $1.0\times10^{-3}$ to $15.0\times10^{-3}$ in a case of a non-magnetic toner and also has a dielectric dissipation factor of from $2\times10^{-3}$ to $30\times10^{-3}$ in a case of a magnetic toner although it varies depending on a content and a kind of a magnetic powder used. The volume resistivity of the toner is measured by pressure-molding toner particles into a disk-like test piece having a diameter of 50 mm and a thickness of 2 mm, fixing the test piece on an electrode for solid, and measuring a dielectric dissipation factor (Tan δ) value obtained by applying a frequency of 1 KHz and a peak to peak voltage of 0.1 KV by using a LCR meter (4284A manufactured by Hughlet Packard Co.).

The toner of the present invention preferably has an Izod impact strength of from 0.1 to 30 kg·cm/cm. The Izod impact strength of the toner is measured by subjecting a plate-like test piece prepared by heat-melting toner particles to a test of JIS standard K-7110 (impact strength test method of rigid plastic).

The toner of the present invention preferably has a melt index (MI value) of from 10 to 150 g/10 min. The melt index (MI value) of the toner is measured at a temperature of 125° C. under a load of 10 kg in accordance with JIS standard K-7210 (A method).

The toner of the present invention preferably has a melting-initiating temperature in a range of from 80 to 180° C., and also has a 4 mm-offset temperature in a range of from 90 to 220° C. The melt-initiating temperature of the toner is measured by pressure-molding toner particles into a cylindrical test piece having a diameter of 10 mm and a thickness of 20 mm, setting the test piece in a heat-melting property-measuring apparatus, e.g. a flow tester (CFT-500C manufactured by Shimadzu Seisakusyo K.K.) and measuring a temperature value, at which a piston begins to descend under a load of $196\times10^4$ Pa (20 kgf/cm²) at the initiation of melting. The 4 mm descending temperature of the toner is measured by measuring a temperature value, at which a piston descends 4 mm in the same test as above.

The toner of the present invention preferably has a glass transition temperature (Tg) in a range of from 35 to 80° C., more preferably in a range of from 40 to 75° C. The glass transition temperature of the toner is measured from a peak value of a phase change appeared when raising a temperature at a constant rate, rapidly cooling and raising a temperature again by using a differential thermogravimetry apparatus (DSC). When the Tg value of the toner is lower than 35° C., an offset resistance and a storage stability become poor and when the Tg value exceeds 80° C., a fixing strength of an image is lowered.

It is preferable that the toner of the present invention provides a peak-top temperature of the maximum peak in a zone of 70 to 120° C. in the heat-absorption peak observed by DSC measurement.

The electrostatic image developing toner of the present invention preferably has a melt viscosity in a range of from 100 to 500 Pa·s (from 1,000 to 50,000 poises), more preferably from 150 to 3,800 Pa·s (from 1,500 to 38,000 poises). The melt viscosity of the toner is measured by pressure-molding toner particles into a cylindrical test piece having a diameter of 10 mm and a thickness of 20 mm, setting the test piece in a heat melt property-measuring apparatus, e.g. a flow tester (CFT-500C manufactured by Shimadzu Seisakusyo K.K.), and measuring the melt viscosity under a load of $196\times10^4$ Pa (20 kgf/cm²)

It is preferable that a monoazo iron complex compound as a charge controlling agent of the present invention should be present on a surface of a toner in an amount of at least 1 mg per 1 g of the toner. The amount of the monoazo iron complex compound present on the toner surface is determined by fully washing the monoazo iron complex compound on the toner surface with an organic solvent such as methyl alcohol dissolving only the monoazo iron complex compound and not dissolving a resin, a coloring agent and a wax of the toner and measuring a concentration of the washing solution in accordance with a calorimetric method with a previously prepared analytical curve using an absorptiometric spectrophotometer or the like.

A monoazo iron complex compound present on a surface of the toner of the present invention preferably has a volume base average particle size of from 0.05 μm to 3 μm, preferably from 0.1 μm to 1 μm.

If the average particle size of the charge controlling agent on the toner surface is smaller than 0.05 μm, the charge controlling agent can not sufficiently achieve its effect, and if the average particle size exceeds 3 μm, the charge controlling agent tends to be dropped in a larger amount at the time of charging, to lower a charged amount by contaminating a carrier, to cause fogging due to an increase of reverse-polar toner particles and to cause flying of toner particles within a copying machine.

A particle size of a monoazo iron complex compound present on a toner surface can be measured in the following manner. First, a predetermined amount of a toner is made into a thin film by heat-melting, and the thin film is enlarged about 500 times in an image by a polarizing microscope (BH-2, manufactured by Olympus Optical Co., Ltd.) equipped with a CCD camera in such a manner as to be able to recognize monoazo iron complex compound particles only in the toner. The enlarged image thus obtained is transferred to an image analyzing apparatus (Luzex FS® manufactured by Nireko K.K.), to calculate a particle distribution of the monoazo iron complex compound particles by image analysis. Also, in the same manner as above, a toner from which a monoazo iron complex compound only is extracted from a toner surface is made into a thin film by heat-melting, and its particle size distribution is measured. Judging from a difference between a particle size distribution of a monoazo iron complex compound present in the whole toner and a particle size distribution of a monoazo iron complex compound present only in the toner inside, a particle size distribution of a monoazo iron complex compound present on the toner surface is determined, and its average particle size is defined as an average particle size of a monoazo iron complex compound present on the toner surface.

A solvent-undissolved remaining content of the toner of the present invention is preferably in a range of from 0 to 30 mass % as a content insoluble in tetrahydrofuran (THF), in a range of from 0 to 40 mass % as a content insoluble in ethyl acetate and in a range of from 0 to 30 mass % as a content insoluble in chloroform. The solvent-undissolved remaining content is measured by uniformly dissolving or dispersing 1 g of a toner respectively 100 me of each of tetrahydrofuran (THF), ethyl acetate and chloroform, pressure-filtrating the solution or the dispersion, drying the filtrate to carry out quantitative determination, and calculating a percentage of an insoluble material of the toner, which is insoluble in an organic solvent.

The toner of the present invention can be used for one-component developing system which is one of image-forming methods. The one-component developing system is a system of developing a latent image by applying a thin toner film to a latent image-supporting element. The thin toner film is formed by an apparatus equipped with a toner-transporting element, a toner layer thickness-adjusting element and a tone-supplying element, wherein the toner-supplying element and the toner-transporting element as well as the toner layer thickness-adjusting element and the toner-transporting element are respectively in contact therewith.

A two-component developing system of using the toner of the present invention is concretely described hereinafter. The two-component developing system employs a toner and a carrier (having functions as a charge-imparting material and a toner-conveying material), and examples of the carrier used include a magnetic material, glass beads and the like. By stirring a developer (a toner and a carrier) by a developer-stirring element, a predetermined charge amount is generated and is conveyed by a magnet roller to a part where development is carried out. By a magnetic force of the magnet roller, the developer is retained on the surface of the roller, and the developer is formed into a layer of appropriate height restricted by a developer-restricting plate forming a magnetic brush. The developer moves on the roller in accordance with rotation of a developing roller in a contact state with an electrostatic latent image-holding material or in non-contact state at a predetermined distance so as to be faced to the electrostatic latent image-holding material, and the latent image is developed into a visible image. In the development in the non-contact state, it is usual to produce a direct current electric field between the developer and the latent image-holding material, thereby providing a driving force for flying the toner between a predetermined distance space, or an alternating current field may be produced in order to make a clearer image.

Also, the charge controlling agent of the present invention is suitable as a charge controlling agent (charge-enhancing agent) in a paint for electrostatic painting. Thus, the paint for electrostatic painting containing the charge-enhancing agent is excellent in environmental resistance, storage stability, particularly thermostability and durability, and has a painting efficiency reaching 100%, and forms a thick film having no defects.

Further, it is quite effective to add the charge controlling agent of the present invention to a carrier-coating agent for two-component developing system. In this case, an electrostatic charge imparted to a toner becomes a positively charged type which is a reverse charge of a case of a usual charge, but the charge controlling agent of the present invention having an excellent quick chargeability (quick charge up speed) can achieve a charge-imparting effect from the carrier side as well as a charge controlling effect having a satisfactory quick chargeability in the same manner as at the time of using a toner. Also, the charge controlling agent of the present invention provides excellent thermostability, fastness and long term running properties (printing resistance).

EXAMPLES

Hereinafter, the present invention is illustrated with reference to Examples, but should not be limited thereto. In the Examples, "part" means "mass part".

Preparation Example 1 (Preparation Example of Compound No. 1 in Table 1)

10 parts of 4-chloro-2-aminophenol was added to 76.5 parts of water and 15.2 parts of 35% hydrochloric acid, and was dissolved by stirring under cooling. 13.6 parts of sodium nitrite dissolved in 24.6 parts of water was dropwise added to the above hydrochloric aqueous solution at an inner temperature of at most 10° C., and the temperature was maintained at 5 to 10° C. optionally by adding 10 parts of crushed ice. After finishing the dropwise adding, the resultant mixture was stirred and reacted at 10° C. for 2 hours. After adding 0.2 part of sulfamic acid thereto to react the mixture for 10 minutes, it was confirmed by a potassium iodide starch paper that an excess amount of nitrous acid did not remain, thus preparing a diazonium solution.

Thereafter, 12.0 parts of 3-methyl-1-phenyl-5-pyrazolone was added to a mixture of 87 parts of water, 12.1 parts of 25% sodium hydroxide, 4.9 parts of sodium carbonate and 104.6 parts of n-butanol, and was dissolved therein under stirring at room temperature. The above prepared diazonium solution was then added thereto to carry out coupling reaction by stirring at 20 to 22° C. for 4 hours. After 4 hours, the reaction was finished by confirming that the reaction with resorcin did not occur any further. After adding 30.4 parts of water thereto, the resultant reaction mixture was fully stirred and was allowed to stand to separate a lower aqueous layer. Further, 92.8 parts of water and 8.7 parts of 25% sodium hydroxide were added thereto to carry out washing under stirring, and a lower aqueous layer was separated.

42.2 parts of water, 5.9 parts of salicylic acid, 24.6 parts of n-butanol and 48.5 parts of 15% sodium carbonate were added to the above prepared reaction solution, and the mixture was stirred. 15.1 parts of 38% ferric chloride aqueous solution and 48.5 parts of 15% sodium carbonate were added thereto, and after raising an inner temperature to 30° C., complex-forming reaction was carried out by stirring for 8 hours. After 8 hours, the reaction was finished by confirming disappearance of a starting material spot by TLC. After stopping the stirring, the reaction solution was allowed to stand to separate a lower aqueous layer. Further, 92.8 parts of water, 12.3 parts of n-butanol and 8.7 parts of 25% sodium hydroxide were added thereto, and washing was carried out by stirring, and a lower aqueous layer was separated. After filtrating to recover an iron complex compound, the product was washed with 253 parts of water.

5.9 parts of ammonium sulfate was added to 82.3 parts of water, and the mixture was stirred while raising a temperature. When an inner temperature reached 90° C., a mixture solution having the above prepared iron complex compound dispersed in 113.9 parts of water was dropwise added thereto by a pipet. The resultant mixture was stirred for 1 hour while removing n-butanol by distillation at 97° C. to 99° C. After filtrating under cooling, a filter cake was washed with 253 parts of water. The cake was dried under vacuum at 60° C., and after confirming that the weight of the product reached a constant level, 24.8 parts of an aimed compound was obtained.

The compound thus obtained was subjected to infrared absorption spectrum, visible light absorption spectrum, element analysis (C, H, N), atomic absorption analysis and mass spectrum, and it was confirmed that the product was compound No. 1.

The infrared absorption spectrum was carried out by tablet method (KBr). Hereinafter, the infrared absorption spectrum was carried out by the same method.

Preparation Example 2 (Preparation Example of Compound No. 2 in Table 1)

10 parts of 4-chloro-2-aminophenol was added to 76.5 parts of water and 15.2 parts of 35% hydrochloric acid, and was dissolved by stirring under cooling. 13.6 parts of sodium nitrite dissolved in 24.6 parts of water was dropwise added to the above hydrochloric aqueous solution at an inner temperature of at most 10° C., and the temperature was maintained at 5 to 10° C. optionally by adding 10 parts of crushed ice. After finishing the dropwise adding, the resultant mixture was stirred and reacted at 10° C. for 2 hours. After adding 0.2 part of sulfamic acid thereto to react the mixture for 10 minutes, it was confirmed by a potassium iodide starch paper that an excess amount of nitrous acid did not remain, thus preparing a diazonium solution.

Thereafter, 14.4 parts of 3-methyl-1-(4-chlorophenyl)-5-pyrazolone was added to a mixture of 87 parts of water, 12.1 parts of 25% sodium hydroxide, 4.9 parts of sodium carbonate and 104.6 parts of n-butanol, and was dissolved therein under stirring at room temperature. The above prepared diazonium solution was then added thereto to carry out coupling reaction by stirring at 20 to 22° C. for 4 hours. After 4 hours, the reaction was finished by confirming that the reaction with resorcin did not occur any further. After adding 30.4 parts of water thereto, the resultant reaction mixture was fully stirred and was allowed to stand to separate a lower aqueous layer. Further, 92.8 parts of water and 8.7 parts of 25% sodium hydroxide were added thereto to carry out washing under stirring, and a lower aqueous layer was separated.

42.2 parts of water, 5.9 parts of salicylic acid, 24.6 parts of n-butanol and 48.5 parts of 15% sodium carbonate were added to the above prepared reaction solution, and the mixture was stirred. 15.1 parts of 38% ferric chloride aqueous solution and 48.5 parts of 15% sodium carbonate were added thereto, and after raising an inner temperature to 30° C., complex-forming reaction was carried out by stirring for 8 hours. After 8 hours, the reaction was finished by confirming disappearance of a starting material spot by TLC. After stopping stirring, the reaction solution was allowed to stand to separate a lower aqueous layer. Further, 92.8 parts of water, 12.3 parts of n-butanol and 8.7 parts of 25% sodium hydroxide were added thereto, and washing was carried out by stirring, and a lower aqueous layer was separated. After filtrating to recover an iron complex compound, the product was washed with 253 parts of water.

5.9 parts of ammonium sulfate was added to 82.3 parts of water, and the mixture was stirred while raising a temperature. When an inner temperature reached 90° C., a mixture solution having the above prepared iron complex compound dispersed in 113.9 parts of water was dropwise added thereto by a pipet. The resultant mixture was stirred for 1 hour while removing n-butanol by distillation at 97° C. to 99° C. after filtrating under cooling, a filter cake was washed with 253 parts of water. The cake was dried under vacuum at 60° C., and after confirming that the weight of the product reached a constant level, 27.1 parts of an aimed compound was obtained.

The compound thus obtained was subjected to infrared absorption spectrum, visible light absorption spectrum, element analysis (C, H, N), atomic absorption analysis and mass spectrum, and it was confirmed that the product was compound No. 2.

Preparation Example 3 (Preparation Example of Compound No. 3 in Table 1)

10 parts of 4-chloro-2-aminophenol was added to 76.5 parts of water and 15.2 parts of 35% hydrochloric acid, and was dissolved by stirring under cooling. 13.6 parts of sodium nitrite dissolved in 24.6 parts of water was dropwise added to the above hydrochloric aqueous solution at an inner temperature of at most 10° C., and the temperature was maintained at 5 to 10° C. optionally by adding 10 parts of crushed ice. After finishing the dropwise adding, the resultant mixture was reacted at 10° C. for 2 hours. After adding 0.2 part of sulfamic acid thereto to react the mixture for 10 minutes, it was confirmed by a potassium iodide starch paper that an excess amount of nitrous acid did not remain, thus preparing a diazonium solution.

Thereafter, 14.4 parts of 3-methyl-1-(4-chlorophenyl)-5-pyrazolone was added to a mixture of 87 parts of water, 12.1 parts of 25% sodium hydroxide, 4.9 parts of sodium carbonate and 104.6 parts of n-butanol, and was dissolved therein under stirring at room temperature. The above prepared diazonium solution was then added thereto to carry out coupling reaction by stirring at 20 to 22° C. for 4 hours. After 4 hours, the reaction was finished by confirming that the reaction with resorcin did not occur any further. After adding 30.4 parts of water thereto, the resultant reaction mixture was fully stirred and was allowed to stand to separate a lower aqueous layer. Further, 92.8 parts of water and 8.7 parts of 25% sodium hydroxide were added thereto to carry out washing under stirring, and a lower aqueous layer was separated.

42.2 parts of water, 5.9 parts of salicylic acid, 24.6 parts of n-butanol and 48.5 parts of 15% sodium carbonate were added to the above prepared reaction solution, and the mixture was stirred. 15.1 parts of 38% ferric chloride aqueous solution and 18.0 parts of 15% sodium carbonate were added thereto, and pH was adjusted to 4.5 by acetic acid. After raising an inner temperature to 30° C., complex-forming reaction was carried out by stirring for 8 hours. After 8 hours, the reaction was finished by confirming disappearance of a starting material spot by TLC. After stopping the stirring, the reaction solution was allowed to stand to separate a lower aqueous layer. Further, 189.9 parts of water was added thereto, and washing was carried out by stirring, and a lower aqueous layer was separated. After filtrating, a filter cake was washed with 253 parts of water. The cake was dried under vacuum at 60° C., and after confirming that the weight of the product reached a constant level, 26.5 parts of an aimed compound was obtained.

The compound thus obtained was subjected to infrared absorption spectrum, visible light absorption spectrum, element analysis (C, H, N), atomic absorption analysis and mass spectrum, and it was confirmed that the product was compound No. 3.

Preparation Example 4 (Preparation Example of Compound No. 4 in Table 1)

10 parts of 4-chloro-2-aminophenol was added to 76.5 parts of water and 15.2 parts of 35% hydrochloric acid, and was dissolved by stirring under cooling. 13.6 parts of sodium nitrite dissolved in 24.6 parts of water was dropwise added to the above hydrochloric aqueous solution at an inner temperature of at most 10° C., and the temperature was maintained at 5 to 10° C. optionally by adding 10 parts of crushed ice. After finishing the dropwise adding, the resultant mixture was reacted at 10° C. for 2 hours. After adding 0.2 part of sulfamic acid thereto to react the mixture for 10 minutes, it was confirmed by a potassium iodide starch paper that an excess amount of nitrous acid did not remain, thus preparing a diazonium solution.

Thereafter, 12.0 parts of 3-methyl-1-phenyl-5-pyrazolone was added to a mixture of 87 parts of water, 12.1 parts of 25% sodium hydroxide, 4.9 parts of sodium carbonate and 104.6 parts of n-butanol, and was dissolved therein under stirring at room temperature. The above prepared diazonium solution was then added thereto to carry out coupling reaction by stirring at 20 to 22° C. for 4 hours. After 4 hours, the reaction was finished by confirming that the reaction with resorcin did not occur any further. After adding 30.4 parts of water thereto, the resultant reaction mixture was fully stirred and was allowed to stand to separate a lower aqueous layer. Further, 92.8 parts of water and 8.7 parts of 25% sodium hydroxide were added thereto to carry out washing under stirring, and a lower aqueous layer was separated.

42.2 parts of water, 5.9 parts of salicylic acid, 24.6 parts of n-butanol and 48.5 parts of 15% sodium carbonate were added to the above prepared reaction solution, and the mixture was stirred. 15.1 parts of 38% ferric chloride aqueous solution and 18.0 parts of 15% sodium carbonate were added thereto, and pH was adjusted to 4.5 by acetic acid. After raising an inner temperature to 30° C., complex-forming reaction was carried out by stirring for 8 hours. After 8 hours, the reaction was finished by confirming disappearance of a starting material spot by TLC. After stopping the stirring, the reaction solution was allowed to stand to separate a lower aqueous layer. Further, 189.9 parts of water was added thereto, and washing was carried out by stirring, and a lower aqueous layer was separated. After filtrating, a filter cake was washed with 253 parts of water. The cake was dried under vacuum at 60° C., and after confirming that the weight of the product reached a constant level, 24.2 parts of an aimed compound was obtained.

The compound thus obtained was subjected to infrared absorption spectrum, visible light absorption spectrum, element analysis (C, H, N), atomic absorption analysis and mass spectrum, and it was confirmed that the product was compound No. 4.

Also, compounds Nos. 5 to 20 and compound No. 22 in Table 1 and Table 2 were prepared in the same manner as in Preparation Examples 1 to 4.

Compound No. 21 was prepared in the same manner as in Preparation Example 2, except that the amount of ammonium sulfate used in Preparation Example 2 was made half.

Comparative Charge Controlling Agent 1

Iron azo complex having the following structure which is a known charge controlling agent (trade name: T-77, manufactured by Hodogaya Chemical Co., Ltd.). In the following formula, a+b+c is 1.

Formula 11

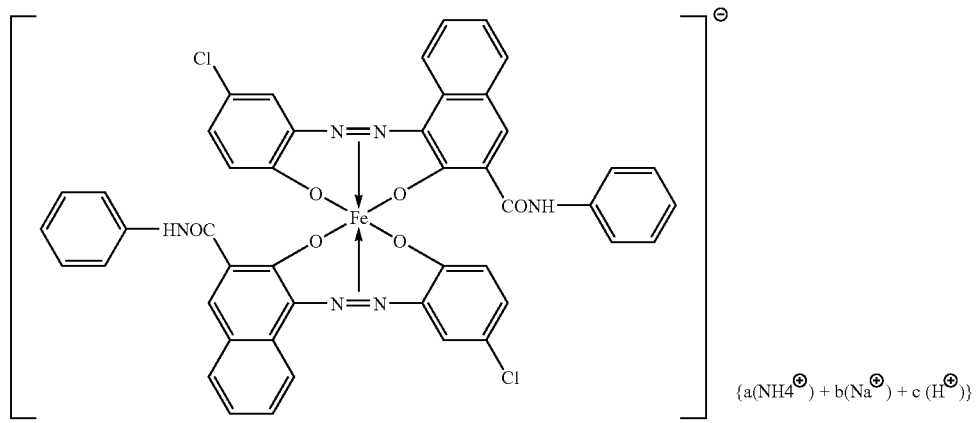

Comparative Charge Controlling Agent 2

Chromium azo complex having the following structure which is a known charge controlling agent (trade name: T-95, manufactured by Hodogaya Chemical Co., Ltd.).

Formula 12

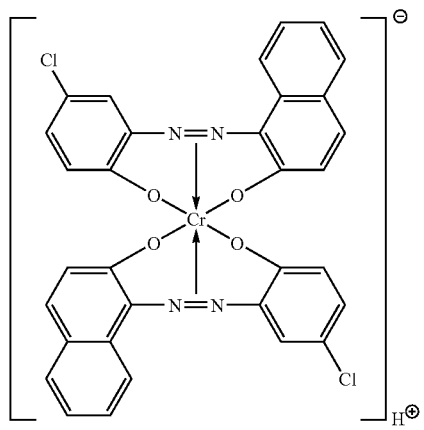

Comparative Charge Controlling Agent 3

Comparative charge controlling agent 3 was prepared in the following manner.

0.4 mol of 3,5-di-tert-butylsalicylic acid was added to 0.5 mol of sodium hydroxide and water, and was dissolved by heating. 0.1 mol of $Al_2(SO_4)_3$ aqueous solution was added to this solution to carry out reaction. After reacting at 50° C. for 3 hours, a precipitated white crystal was recovered by filtration. The white crystal thus obtained was washed with water, and was dried under a reduced pressure at 40° C. for 24 hours. The reaction product thus obtained was an aimed compound having 2 molecules of 3,5-di-tert-butylsalicylic acid bonded to an aluminum atom.

Example 1

| | |
|---|---|
| Styrene-acrylic copolymer resin (acid value 0.1 mgKOH/g) (Trade name, CPR-100, manufactured by Mitsui Chemicals, Inc.) | 91 parts |
| Compound No. 1 obtained in Preparation Example 1 | 1 part |
| Carbon black (Trade name, MA-100, manufactured by Mitsubishi Chemical Corporation) | 5 parts |
| Low molecular weight polypropylene (Trade name, Biscoal 550P, manufactured by Sanyo Kasei K.K.) | 3 parts |

The above mixture was melt-mixed at 130° C. in a heat-mixing apparatus (biaxial extrusion kneader), and the cooled mixture was roughly pulverized by a hammer mill. The mixture was further finely pulverized by a jet mill, and the pulverized product was classified to obtain a non-magnetic toner having a volume average particle size of 9±0.5 μm. 4 parts of the above obtained toner was mixed with 100 parts of a silicon coated type ferrite carrier (trade name, F96-100, manufactured by Powder Tech K.K.), and the toner thus mixed was shaken to have the toner negatively charged, and the toner thus obtained was measured by a blow-off powder charged amount-measuring apparatus.

Also, a time constant (τ) which is in index for a quick chargeability was calculated. Time constant (τ) was determined by measuring a charged amount until reaching a saturated charge for every certain time by a blow-off charged amount-measuring apparatus, calculating in (qmax-q) in accordance with the following formula (disclosed in "Denshi Shashin Gakkaishi, P307, Vol 27, No. 3, (1988)") and plotting the relation between time t and ln (qmax-q) in a graph.

$$(qmax-q)/(qmax-q0)=\exp(-t/\tau)$$

In the above formula, qmax represents a saturated charged amount, q0 represents an initial charged amount (at a charging time of 10 seconds), t represents each measuring time and q represents a charged amount at that time.

When a quick chargeability is good, a time constant becomes a small value. The unit of time constant is second.

Also, an environmental stability of charging was evaluated. The environmental stability of charging was evaluated by measuring a charged amount under a usual environment of 25° C. -50% RH (relative humidity), and also measuring a charged amount under a low humidity environment (10° C. -30% RH) and a high humidity environment (35° C. -85% RH). The measurement of charged amount was carried out by fully charging a developer exposed under each environment for 24 hours, and measuring a saturated charged amount by a blow-off charged amount-measuring apparatus. As a result of measurement under the above three environments, a case of a change in a charged amount being less than 10% is defined as good (○), a case of a change in a charged amount being from 10 to 20% is defined as slightly bad (Δ) and a case of a change in a charged amount being exceeding 20% is defined as bad (X). The results of a charged amount, a time constant and an environmental stability are shown in the following Table 3.

Examples 2 to 22

A non-magnetic toner was prepared in the same manner as in Example 1, except that "compound No. 1 obtained in Preparation Example 1" was replaced by each of compounds Nos. 2 to 22 in Tables 1 and 2, and was evaluated with respect to a charged amount, a time constant and an environmental stability by a blow-off powder charged amount-measuring apparatus. The results of these Examples 2 to 22 are shown in the following Table 3.

Comparative Examples 1 to 3

A comparative non-magnetic toner was prepared in the same manner as in Example 1, except that "compound No. 1 obtained in Preparation Example 1" was replaced by each of comparative charge controlling agent 1, comparative charge controlling agent 2 and comparative charge controlling agent 3, and was evaluated with respect to a charged amount, a time constant and an environmental stability by a blow-off powder charged amount-measuring apparatus. The results of these Comparative Examples 1 to 3 are shown in the following Table 3.

TABLE 3

|  | Charged amount (μC/g) | Time constant τ (s) | Environmental stability |
|---|---|---|---|
| Example 1 | −15.5 | 93 | ○ |
| Example 2 | −17.6 | 83 | ○ |
| Example 3 | −20.9 | 74 | ○ |
| Example 4 | −16.8 | 71 | ○ |
| Example 5 | −17.0 | 109 | ○ |
| Example 6 | −16.8 | 110 | ○ |
| Example 7 | −17.4 | 116 | ○ |
| Example 8 | −15.7 | 124 | ○ |
| Example 9 | −17.0 | 114 | ○ |
| Example 10 | −15.9 | 101 | ○ |
| Example 11 | −15.6 | 137 | ○ |
| Example 12 | −15.2 | 119 | ○ |
| Example 13 | −15.3 | 117 | ○ |
| Example 14 | −16.7 | 139 | ○ |
| Example 15 | −18.1 | 88 | ○ |
| Example 16 | −17.9 | 130 | ○ |
| Example 17 | −18.0 | 124 | ○ |
| Example 18 | −17.5 | 85 | ○ |
| Example 19 | −16.5 | 81 | ○ |
| Example 20 | −16.3 | 95 | ○ |
| Example 21 | −17.8 | 85 | ○ |
| Example 22 | −16.3 | 113 | ○ |
| Comparative Example 1 | −16.3 | 286 | Δ |
| Comparative Example 2 | −19.7 | 245 | ○ |
| Comparative Example 3 | −7.9 | 225 | X | ing system, which was remodeled so as to be able to optionally control a surface potential of a photosensitive material, a voltage applied to a developing roller, a voltage of transferring and a fixing temperature, and each condition was determined so as to make the best printing at the initial image. The evaluation of image properties was carried out by printing with a toner continuously supplied and sampling a 10th printed sheet (initial image), a 5,000th sheet after continuous printing and a 20,000th printed sheet after initiating test chart printing (see Examples 23 to 26 and Comparative Examples 4 to 6).

An image density was measured by using a plain paper (75 g/m$^2$), sampling a printed sheet after printing a predetermined number of sheets, and measuring a density of a black solid printed part of the sampled printed sheet by a Macbeth reflection densitometer (RD-918, manufactured by Sakata Inks K.K.). A fog density was determined by measuring a reflection density of a non-printed part and deducting a reflection density (0.05) of the plain paper before printing as a base value from the above measured reflection density value. A thin line reproducibility was evaluated as to whether thin lines of 30 μm on a test chart could be faithfully reproduced or not. The results are shown in the following Table 4. In the following Table 4, a thin line reproducibility was expressed by "good" when thin lines were faithfully reproduced and expressed by "no good" when thin lines were not faithfully reproduced.

TABLE 4

|  | Thin line reproducibility | | | Image density | | | Fog density | | |
|---|---|---|---|---|---|---|---|---|---|
|  | Initial image | After copying 5,000 sheets | After copying 20,000 sheets | Initial image | After copying 5,000 sheets | After copying 20,000 sheets | Initial image | After copying 5,000 sheets | After copying 20,000 sheets |
| Ex. 23 | Good | Good | Good | 1.45 | 1.45 | 1.45 | 0.01 | 0.00 | 0.01 |
| Ex. 24 | Good | Good | Good | 1.44 | 1.45 | 1.43 | 0.01 | 0.01 | 0.02 |
| Ex. 25 | Good | Good | Good | 1.45 | 1.44 | 1.45 | 0.01 | 0.02 | 0.03 |
| Ex. 26 | Good | Good | Good | 1.45 | 1.44 | 1.44 | 0.01 | 0.01 | 0.02 |
| Comp. Ex. 4 | Good | Good | No good | 1.40 | 1.35 | 1.31 | 0.02 | 0.06 | 0.07 |
| Comp. Ex. 5 | Good | Good | No good | 1.41 | 1.42 | 1.29 | 0.01 | 0.03 | 0.10 |
| Comp. Ex. 6 | Good | No good | No good | 1.38 | 1.34 | 1.18 | 0.02 | 0.04 | 0.12 |

As evident from the above Table 3, the non-magnetic toners of Examples 1 to 22 provided practically sufficient charged amounts, and since time constant values were low, it is proved that their toners having an excellent quick chargeability, an excellent environmental stability and a high charging performance.

(Evaluation of Image Properties in Accordance with Non-magnetic Two-component Developing Method)

A developer was prepared by mixing 4 parts of a toner of each of Examples 1 to 4 and Comparative Examples 1 to 3 with 100 parts of a silicon coated type ferrite carrier (trade name, F96-100, manufactured by Powder Tech K.K.), and image properties of the toners thus prepared were evaluated in accordance with non-magnetic two-component developing system. An image-forming apparatus used in the evaluation of the image properties was a commercially available copying machine of non-magnetic two-component develop- Examples 23 to 26 provided an image density in a range of from 1.40 to 1.45 which is considered to be desirable in this copying machine. Also, the image density was not substantially changed and was stable during long term continuous printing. Further, a fog density value was quite low, and did not increase during continuous printing. Also, a thin line reproducibility was good and stable.

Comparative Examples 4 to 6 provided a satisfactory image at the initial stage, but an image density was somewhat lowered and a fog density was raised after continuously printing 5,000 sheets. These image degradations became further severe and remarkable after continuously printing 20,000 sheets, and reached a troublesome level. Also, a thin line reproducibility was severely degraded by long term continuous printing.

Example 27

| | |
|---|---|
| Styrene-acrylic copolymer resin (acid value 0.1 mgKOH/g) (Trade name, CPR-100, manufactured by Mitsui Chemicals, Inc.) | 100 parts |
| Compound No. 1 obtained in Preparation Example 1 | 2 parts |
| Magnetic iron oxide (Trade name, BL-200, manufactured by Titan Kogyo K.K.) | 90 parts |
| Low molecular weight polypropylene (Trade name, Biscoal 550P, manufactured by Sanyo Kasei K.K.) | 3 parts |

The above mixture was melt-mixed at 130° C. in a heat-mixing apparatus (biaxial extrusion kneader), and the cooled mixture was roughly pulverized by a hammer mill. The pulverized product was further finely pulverized by a jet mill, and was classified to obtain a magnetic toner having a volume average particle size of 9±0.5 µm.

Examples 28 to 30

A magnetic toner was prepared in the same manner as in Example 27, except that "compound No. 1 obtained in Preparation Example 1" was replaced by each of "compound No. 2 obtained in Preparation Example 2", "compound No. 3 obtained in Preparation Example 3" and "compound No. 4 obtained in Preparation example 4", and they are respectively Example 28, Example 29 and Example 30.

Comparative Examples 7 to 9

A comparative magnetic toner was prepared in the same manner as in Example 27, except that "compound No. 1 obtained in Preparation Example 1" was replaced by each of comparative charge controlling agent 1, comparative charge controlling agent 2 and comparative charge controlling agent 3, and they are respectively Comparative Examples 7 to 9.

(Evaluation of Image Properties in Accordance with Magnetic One-component Developing System)

Image properties of toners prepared in Examples 27 to 30 and Comparative Examples 7 to 9 were evaluated in accordance with magnetic one-component developing system.

An image-forming apparatus used to carry out the evaluation of image properties was a commercially available printer of magnetic one-component developing system (resolving power 600 dpi) which was remodeled so as to be able to control a surface potential of a photosensitive material, a voltage applied to a developing roller, a voltage of transferring and a fixing temperature, and each condition was determined so as to make the best printing at the initial image.

Printing was carried out by continuously supplying a toner and forwarding a test chart from a personal computer. The evaluation of image properties was carried out by sampling a 10th printed sheet (initial image) from the initiation of printing, a 1,000th continuously printed sheet and a 5,000th continuously printed sheet.

An image density was measured by sampling an image on a plain paper (75 g/m$^2$) after printing a predetermined number of sheets, and measuring a density of a black solid printed part by a Macbeth reflection densitometer (RD-918, manufactured by Sakata Inks K.K.). Also, a fog density was determined by measuring a reflection density of a non-printed part and deducting a reflection density (0.05) of the plain paper before printing as a base value from the above measured density. A dot reproducibility was evaluated by judging as to whether dots of a test chart were faithfully reproduced or not, and the dot reproducibility was judged as to whether an independent dot pattern of about 50 µm could be reproduced without defect or not. Among about 50 dots, if an amount of defective dots was at least 10%, the dot reproducibility was considered to be no good, whereas if an amount of defective dots was less than 10%, the reproducibility was considered to be good. The results are shown in the following Table 5.

TABLE 5

| | Dot reproducibility | | | Image density | | | Fog density | | |
|---|---|---|---|---|---|---|---|---|---|
| | Initial image | After copying 1,000 sheets | After copying 5,000 sheets | Initial image | After copying 1,000 sheets | After copying 5,000 sheets | Initial image | After copying 1,000 sheets | After copying 5,000 sheets |
| Ex. 27 | Good | Good | Good | 1.45 | 1.46 | 1.45 | 0.00 | 0.00 | 0.00 |
| Ex. 28 | Good | Good | Good | 1.47 | 1.46 | 1.47 | 0.00 | 0.01 | 0.01 |
| Ex. 29 | Good | Good | Good | 1.45 | 1.47 | 1.47 | 0.00 | 0.01 | 0.00 |
| Ex. 30 | Good | Good | Good | 1.46 | 1.45 | 1.45 | 0.00 | 0.01 | 0.01 |
| Comp. Ex. 7 | Good | Good | No good | 1.41 | 1.35 | 1.35 | 0.02 | 0.09 | 0.10 |
| Comp. Ex. 8 | Good | Good | No good | 1.43 | 1.34 | 1.18 | 0.01 | 0.07 | 0.12 |
| Comp. Ex. 9 | Good | No good | No good | 1.39 | 1.37 | 1.22 | 0.00 | 0.06 | 0.11 |

In Examples 27 to 30, an image density was good and was in a range of from 1.45 to 1.55 which is considered to be desirable for a printer. The density was not substantially changed and was stable during long term continuous printing. A fog density value was also quite low, and did not increase during continuous printing. A dot reproducibility was also good and was stable.

In Comparative Examples 7 to 9, a satisfactory image could be obtained at the initial stage, but an image density was lowered and a fog density was raised when 1,000 sheets were continuously printed. Further, these image degradations became remarkable and reached a troublesome level after continuously printing 5,000 sheets. A dot reproducibility was greatly degraded by long term continuous printing.

The entire disclosures of Japanese Patent Application No. 2003-96578 filed on Mar. 31, 2003, Japanese Patent Application No. 2003-201262 filed on Jul. 24, 2003, Japanese Patent Application No. 2003-207208 filed on Aug. 11, 2003 and Japanese Patent Application No. 2003-356674 filed on Oct. 16, 2003 including specifications, claims, drawings and summaries are incorporated herein by reference in their entireties.

What is claimed is:

1. An electrophotographic printing method which comprises using a negatively chargeable toner comprising a charge controlling agent comprising a monoazo iron complex compound of the formula (1) as an effective component,

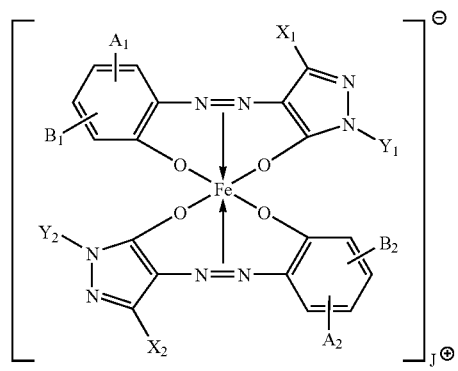

wherein $A_1$, $A_2$, $B_1$ and $B_2$ are respectively independently H, an alkyl group or a halogen atom, J is H, an alkali metal, $NH_4$ or an alkylammonium, they may be two or more kinds, $X_1$ and $X_2$ are respectively independently H, an alkyl group or a halogen atom, and $Y_1$ and $Y_2$ are respectively independently H, an alkyl group or an aromatic group which may have a substituent, provided that a case in which $A_1$, $A_2$, $B_1$, $B_2$, $X_1$, $X_2$, $Y_1$, and $Y_2$ are hydrogen at the same time is excluded.

2. The electrophotographic printing method according to claim 1, wherein the charge controlling agent contains a monoazo iron complex compound of the formula (2) as an effective component,

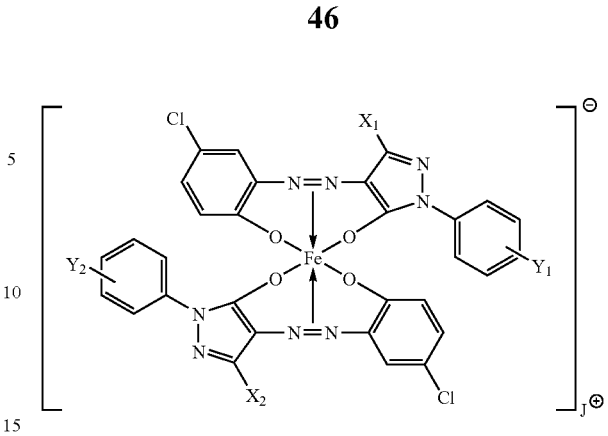

wherein J is H, Na, $NH_4$ or an alkylammonium, they may be two or more kinds, $X_1$ and $X_2$ are respectively independently H, an alkyl group or a halogen atom, and $Y_1$ and $Y_2$ are respectively independently H, an alkyl group or a halogen atom.

3. The electrophotographic printing method according to claim 1, wherein the charge controlling agent contains a monoazo iron complex compound of the formula (3) as an effective component,

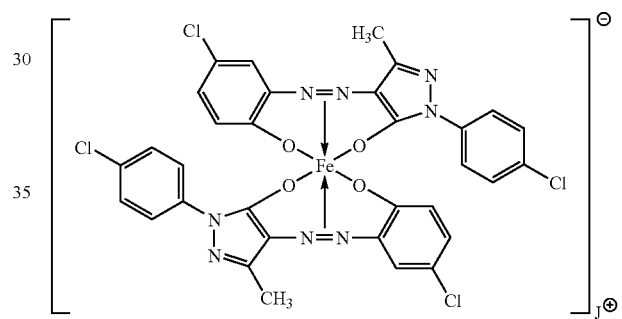

wherein J is H, Na, $NH_4$ or an alkylammonium, and they may be two or more kinds.

4. The electrophotographic printing method according to claim 1, wherein the charge controlling agent contains a monoazo iron complex compound of the formula (4) as an effective component,

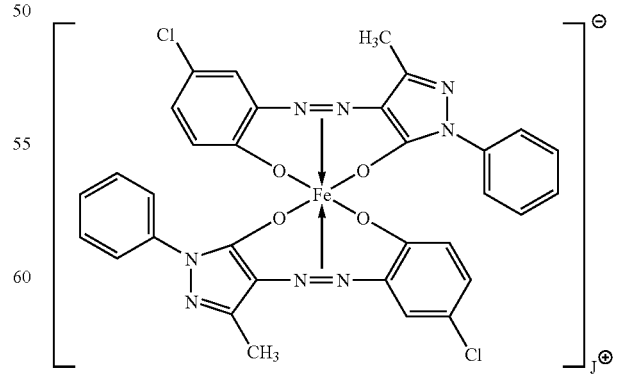

wherein J is H, Na, $NH_4$ or an alkylammonium, and they may be two or more kinds.

5. The electrophotographic printing method according to claim 1, wherein the charge controlling agent contains a monoazo iron complex compound of the formula (5) as an effective component,

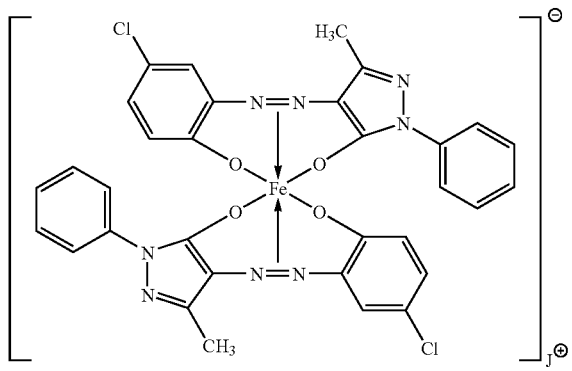

6. The electrophotographic printing method according to any one of claims 1 to 5, wherein the charge controlling agent has a volume average particle size of from 0.1 to 20 μm.

7. A negatively chargeable toner which comprises a charge controlling agent as defined in claim 1, a coloring agent and a binder resin.

8. The toner according to claim 7, wherein the charge controlling agent is defined by the following formula:

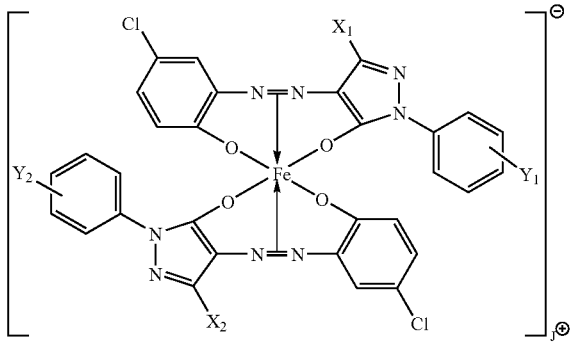

wherein J is H, Na, $NH_4$ or an alkylammonium, they may be two or more kinds, $X_1$ and $X_2$ are respectively independently H, an alkyl group or a halogen atom, and $Y_1$ and $Y_2$ are respectively independently H, an alkyl group or a halogen atom.

9. The toner according to claim 7, wherein the monoazo iron complex compound as an effective component of the charge controlling agent is incorporated within toner particles in an amount of from 0.1 to 10 mass parts per 100 mass parts of a binder resin.

10. The toner according to claim 7, wherein the binder resin has an acid value of from 0.1 to 100 mgKOH/g.

11. The toner according to claim 7, wherein the coloring agent is a magnetic material.

12. The toner according to claim 7, wherein the coloring agent is a non-magnetic coloring agent and is contained in an amount of from 0.1 to 20 mass parts per 100 mass parts of a binder resin.

13. The toner according to claim 7, wherein a wax is further contained.

14. The toner according to claim 7, wherein the toner has a volume average particle size of from 2 to 15 μm.

15. A one-component system developer which comprises the toner as defined in claim 7.

16. A two-component system developer which comprises a negatively chargeable toner and a carrier, wherein the toner contains at least a binder resin, a coloring agent and a monoazo iron complex compound, and the monoazo iron complex compound is a monoazo iron complex compound as an effective component of the charge controlling agent as defined in claim 1.

17. The two-component system developer according to claim 16, wherein the charge controlling agent is defined by the following formula:

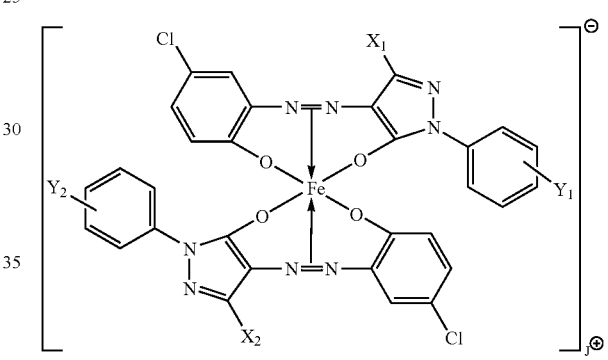

wherein J is H, Na, $NH_4$ or an alkylammonium, they may be two or more kinds. $X_1$ and $X_2$ are respectively independently H, an alkyl group or a halogen atom, and $Y_1$ and $Y_2$ are respectively independently H, an alkyl group or a halogen atom.

18. The two-component system developer according to claim 16, wherein the monoazo iron complex compound is incorporated within toner particles in an amount of from 0.1 to 10 mass parts per 100 mass part of the binder resin.

19. The two-component system developer according to claim 16, wherein the toner contains a styrene-acryl type resin as a binder resin.

20. The two-component system developer according to claim 16, wherein the binder resin has an acid value of from 0.1 to 100 mgKOH/g.

21. The two-component system developer according to claim 16, wherein a wax is further contained.

22. The two-component system developer according to claim 16, wherein the toner has a volume average particle size of from 2 to 15 μm.

23. The two-component system developer according to claim 16, wherein the carrier is a resin-coated carrier.

24. The toner according to claim 7, wherein the charge controlling agent is one as defined in the following formula:

wherein J is H, Na, NH$_4$ or an alkylammonium, and they may be two or more kinds.

25. The toner according to claim 7, wherein the charge controlling agent is defined in the following formula:

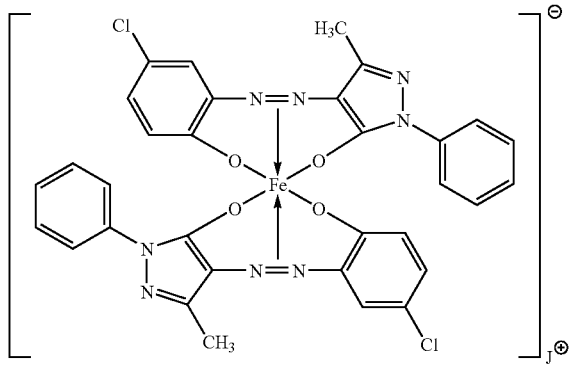

wherein J is H, Na, NH$_4$ or an alkylammonium, and they may be two or more kinds.

26. The toner according to claim 7, wherein the charge controlling agent is defined in the following formula:

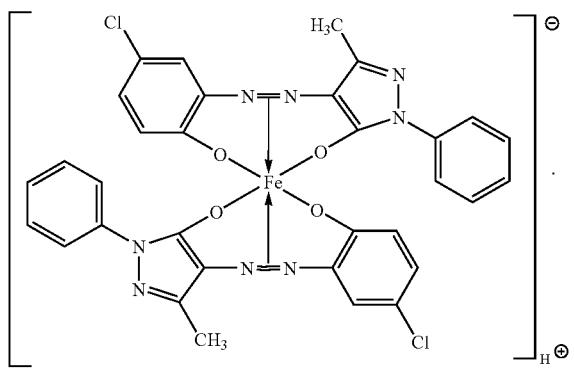

27. The two-component system developer according to claim 16, wherein the charge controlling agent is defined by the following formula:

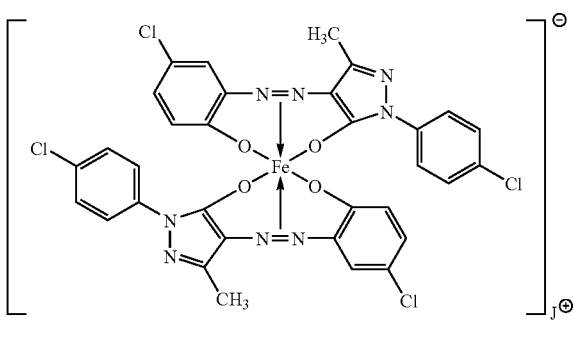

wherein J is H, Na, NH$_4$ or an alkylammonium, and they may be two or more kinds.

28. The two-component system developer according to claim 16, wherein the charge controlling agent is defined by the following formula:

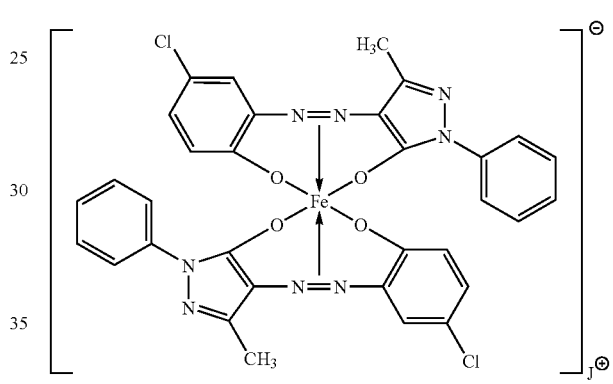

wherein J is H, Na, NH$_4$ or an alkylammonium, and they may be two or more kinds.

29. The two-component system developer according to claim 16, wherein the charge controlling agent is defined by the following formula:

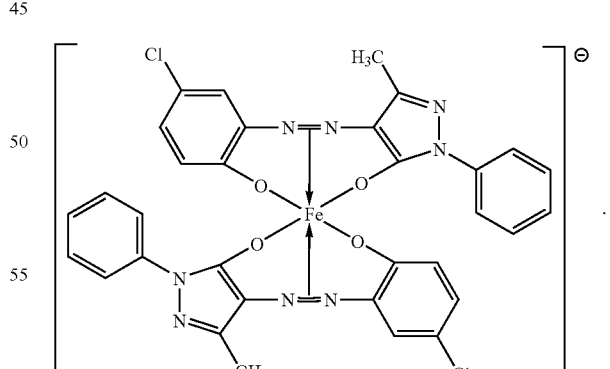

* * * * *